US00RE46412E

(19) United States
(12) Reissued Patent
Desjardins et al.

(10) Patent Number: US RE46,412 E
(45) Date of Reissued Patent: May 23, 2017

(54) METHODS AND SYSTEMS FOR PERFORMING ANGLE-RESOLVED FOURIER-DOMAIN OPTICAL COHERENCE TOMOGRAPHY

(71) Applicants: Adrien Desjardins, London (GB); Benjamin J. Vakoc, Arlington, MA (US); Guillermo J. Tearney, Cambridge, MA (US); Brett Eugene Bouma, Quincy, MA (US)

(72) Inventors: Adrien Desjardins, London (GB); Benjamin J. Vakoc, Arlington, MA (US); Guillermo J. Tearney, Cambridge, MA (US); Brett Eugene Bouma, Quincy, MA (US)

(73) Assignee: THE GENERAL HOSPITAL CORPORATION, Boston, MA (US)

(21) Appl. No.: 14/184,537

(22) Filed: Feb. 19, 2014

Related U.S. Patent Documents

Reissue of:
(64) Patent No.: 7,982,879
Issued: Jul. 19, 2011
Appl. No.: 11/677,278
Filed: Feb. 21, 2007

U.S. Applications:
(60) Provisional application No. 60/776,544, filed on Feb. 24, 2006.

(51) Int. Cl.
*G01B 9/02* (2006.01)
*G01N 21/47* (2006.01)
*A61B 5/00* (2006.01)

(52) U.S. Cl.
CPC ..... *G01N 21/4795* (2013.01); *G01B 9/02043* (2013.01); *G01B 9/02087* (2013.01);
(Continued)

(58) Field of Classification Search
CPC ..... G01N 21/65
(Continued)

(56) References Cited

U.S. PATENT DOCUMENTS 2,339,754 A 1/1944 Brace
3,090,753 A 5/1963 Matuszak et al.
(Continued)

FOREIGN PATENT DOCUMENTS

CN 1550203 12/2004
DE 10351319 6/2005
(Continued)

OTHER PUBLICATIONS

John W. Pyhtila and Adam Wax, "Rapid, depth-resolved light scattering measurements using Fourier domain, angle-resolved low coherence interferometry," Dec. 13, 2004, Optics Express, vol. 12, No. 25, pp. 6178-6183.*
(Continued)

*Primary Examiner* — Christopher E. Lee
(74) *Attorney, Agent, or Firm* — Andrews Kurth Kenyon LLP

(57) ABSTRACT

Arrangements, apparatus and methods are provided according to exemplary embodiments of the present invention. In particular, at least one first electro-magnetic radiation may be received and at least one second electro-magnetic radiation within a solid angle may be forwarded to a sample. The second electro-magnetic radiation may be associated with the first electro-magnetic radiation. A plurality of third electro-magnetic radiations can be received from the sample which is associated with the second electro-magnetic radiation, and at least one portion of the third electro-magnetic radiation is provided outside a periphery of the solid angle. Signals associated with each of the third electro-magnetic radiations can be simultaneously detected, with the signals being associated with information for the sample at a
(Continued)

plurality of depths thereof. The depths can be determined using at least one of the third electro-magnetic radiations without a need to utilize another one of the third electro-magnetic radiations.

14 Claims, 8 Drawing Sheets

(52) U.S. Cl.
CPC ..... *G01B 9/02091* (2013.01); *A61B 5/0073* (2013.01); *G01B 2290/70* (2013.01); *G01N 2021/4714* (2013.01)

(58) Field of Classification Search
USPC ..... 356/301, 445, 446
See application file for complete search history.

(56) References Cited

U.S. PATENT DOCUMENTS 3,601,480 A 8/1971 Randall
3,856,000 A 12/1974 Chikama
3,872,407 A 3/1975 Hughes
3,941,121 A 3/1976 Olinger et al.
3,973,219 A 8/1976 Tang et al.
3,983,507 A 9/1976 Tang et al.
4,030,827 A 6/1977 Delhaye et al.
4,030,831 A 6/1977 Gowrinathan
4,140,364 A 2/1979 Yamashita et al.
4,141,362 A 2/1979 Wurster
4,224,929 A 9/1980 Furihata
4,295,738 A 10/1981 Meltz et al.
4,300,816 A 11/1981 Snitzer et al.
4,303,300 A 12/1981 Pressiat et al.
4,428,643 A 1/1984 Kay
4,479,499 A 10/1984 Alfano
4,533,247 A 8/1985 Epworth
4,585,349 A 4/1986 Gross et al.
4,601,036 A 7/1986 Faxvog et al.
4,607,622 A 8/1986 Fritch et al.
4,631,498 A 12/1986 Cutler
4,639,999 A 2/1987 Daniele
4,650,327 A 3/1987 Ogi
4,734,578 A 3/1988 Horikawa
4,744,656 A 5/1988 Moran et al.
4,751,706 A 6/1988 Rohde et al.
4,763,977 A 8/1988 Kawasaki et al.
4,770,492 A 9/1988 Levin et al.
4,827,907 A 5/1989 Tashiro et al.
4,834,111 A 5/1989 Khanna et al.
4,868,834 A 9/1989 Fox et al.
4,890,901 A 1/1990 Cross, Jr.
4,892,406 A 1/1990 Waters
4,905,169 A 2/1990 Buican et al.
4,909,631 A 3/1990 Tan et al.
4,925,302 A 5/1990 Cutler
4,928,005 A 5/1990 Lefevre et al.
4,940,328 A 7/1990 Hartman
4,965,441 A 10/1990 Picard
4,965,599 A 10/1990 Roddy et al.
4,966,589 A 10/1990 Kaufman
4,984,888 A 1/1991 Tobias et al.
4,993,834 A 2/1991 Carlhoff et al.
4,998,972 A 3/1991 Chin et al.
5,039,193 A 8/1991 Snow et al.
5,040,889 A 8/1991 Keane
5,045,936 A 9/1991 Lobb et al.
5,046,501 A 9/1991 Crilly
5,065,331 A 11/1991 Vachon et al.
5,085,496 A 2/1992 Yoshida et al.
5,120,953 A 6/1992 Harris
5,121,983 A 6/1992 Lee
5,127,730 A 7/1992 Brelje et al.
5,177,488 A 1/1993 Wang et al.
5,197,470 A 3/1993 Helfer et al.
5,202,745 A 4/1993 Sorin et al.
5,202,931 A 4/1993 Bacus
5,208,651 A 5/1993 Buican
5,212,667 A 5/1993 Tomlinson et al.
5,214,538 A 5/1993 Lobb
5,217,456 A 6/1993 Narciso, Jr.
5,228,001 A 7/1993 Birge et al.
5,241,364 A 8/1993 Kimura et al.
5,248,876 A 9/1993 Kerstens et al.
5,250,186 A 10/1993 Dollinger et al.
5,251,009 A 10/1993 Bruno
5,262,644 A 11/1993 Maguire
5,275,594 A 1/1994 Baker et al.
5,281,811 A 1/1994 Lewis
5,283,795 A 2/1994 Fink
5,291,885 A 3/1994 Taniji et al.
5,293,872 A 3/1994 Alfano et al.
5,293,873 A 3/1994 Fang
5,302,025 A 4/1994 Kleinerman
5,304,173 A 4/1994 Kittrell et al.
5,304,810 A 4/1994 Amos
5,305,759 A 4/1994 Kaneko et al.
5,317,389 A 5/1994 Hochberg et al.
5,318,024 A 6/1994 Kittrell et al.
5,321,501 A 6/1994 Swanson et al.
5,333,144 A 7/1994 Liedenbaum et al.
5,348,003 A 9/1994 Caro
5,353,790 A 10/1994 Jacques et al.
5,383,467 A 1/1995 Auer et al.
5,394,235 A 2/1995 Takeuchi et al.
5,400,771 A 3/1995 Pirak et al.
5,404,415 A 4/1995 Mori et al.
5,411,016 A 5/1995 Kume et al.
5,414,509 A 5/1995 Veligdan
5,419,323 A 5/1995 Kittrell et al.
5,424,827 A 6/1995 Horwitz et al.
5,439,000 A 8/1995 Gunderson et al.
5,441,053 A 8/1995 Lodder et al.
5,450,203 A 9/1995 Penkethman
5,454,807 A 10/1995 Lennox et al.
5,459,325 A 10/1995 Hueton et al.
5,459,570 A 10/1995 Swanson et al.
5,465,147 A 11/1995 Swanson
5,479,928 A 1/1996 Cathignoal et al.
5,486,701 A 1/1996 Norton et al.
5,491,524 A 2/1996 Hellmuth et al.
5,491,552 A 2/1996 Knuttel
5,522,004 A 5/1996 Djupsjobacka et al.
5,526,338 A 6/1996 Hasman et al.
5,555,087 A 9/1996 Miyagawa et al.
5,562,100 A 10/1996 Kittrell et al.
5,565,983 A 10/1996 Barnard et al.
5,565,986 A 10/1996 Knuttel
5,566,267 A 10/1996 Neuberger
5,583,342 A 12/1996 Ichie
5,590,660 A 1/1997 MacAulay et al.
5,600,486 A 2/1997 Gal et al.
5,601,087 A 2/1997 Gunderson et al.
5,621,830 A 4/1997 Lucey et al.
5,623,336 A 4/1997 Raab
5,628,313 A 5/1997 Webster, Jr.
5,635,830 A 6/1997 Itoh
5,649,924 A 7/1997 Everett et al.
5,697,373 A 12/1997 Richards-Kortum et al.
5,698,397 A 12/1997 Zarling et al.
5,701,155 A 12/1997 Wood et al.
5,710,630 A 1/1998 Essenpreis et al.
5,716,324 A 2/1998 Toida
5,719,399 A 2/1998 Alfano et al.
5,730,731 A 3/1998 Mollenauer et al.
5,735,276 A 4/1998 Lemelson
5,740,808 A 4/1998 Panescu et al.
5,748,318 A 5/1998 Maris et al.
5,748,598 A 5/1998 Swanson et al.
5,752,518 A 5/1998 McGee et al.
5,784,352 A 7/1998 Swanson et al.
5,785,651 A 7/1998 Kuhn et al.
5,795,295 A 8/1998 Hellmuth et al.

(56) References Cited

U.S. PATENT DOCUMENTS 5,801,826 A 9/1998 Williams
5,801,831 A 9/1998 Sargoytchev et al.
5,803,082 A 9/1998 Stapleton et al.
5,807,261 A 9/1998 Benaron et al.
5,810,719 A 9/1998 Toida
5,817,144 A 10/1998 Gregory
5,829,439 A 11/1998 Yokosawa et al.
5,836,877 A 11/1998 Zavislan
5,840,023 A 11/1998 Oraevsky et al.
5,840,031 A 11/1998 Crowley
5,840,075 A 11/1998 Mueller et al.
5,842,995 A 12/1998 Mahadevan-Jansen et al.
5,843,000 A 12/1998 Nishioka et al.
5,843,052 A 12/1998 Benja-Athon
5,847,827 A 12/1998 Fercher
5,862,273 A 1/1999 Pelletier
5,865,754 A 2/1999 Sevick-Muraca et al.
5,867,268 A 2/1999 Gelikonov et al.
5,871,449 A 2/1999 Brown
5,872,879 A 2/1999 Hamm
5,877,856 A 3/1999 Fercher
5,887,009 A 3/1999 Mandella et al.
5,892,583 A 4/1999 Li
5,910,839 A 6/1999 Erskine et al.
5,912,764 A 6/1999 Togino
5,920,373 A 7/1999 Bille
5,920,390 A 7/1999 Farahi et al.
5,921,926 A 7/1999 Rolland et al.
5,926,592 A 7/1999 Harris et al.
5,949,929 A 9/1999 Hamm
5,951,482 A 9/1999 Winston et al.
5,955,737 A 9/1999 Hallidy et al.
5,956,355 A 9/1999 Swanson et al.
5,968,064 A 10/1999 Selmon et al.
5,975,697 A 11/1999 Podoleanu et al.
5,983,125 A 11/1999 Alfano et al.
5,987,346 A 11/1999 Benaron et al.
5,991,697 A 11/1999 Nelson et al.
5,994,690 A 11/1999 Kulkarni et al.
5,995,223 A 11/1999 Power
6,002,480 A 12/1999 Izatt et al. ..... 356/479
6,004,314 A 12/1999 Wei et al.
6,006,128 A 12/1999 Izatt et al.
6,007,996 A 12/1999 McNamara et al.
6,010,449 A 1/2000 Selmon et al.
6,014,214 A 1/2000 Li
6,016,197 A 1/2000 Krivoshlykov
6,020,963 A 2/2000 DiMarzio et al.
6,025,956 A 2/2000 Nagano et al.
6,033,721 A 3/2000 Nassuphis
6,037,579 A 3/2000 Chan et al.
6,044,288 A 3/2000 Wake et al.
6,045,511 A 4/2000 Ott et al.
6,048,742 A 4/2000 Weyburne et al.
6,052,186 A 4/2000 Tsai
6,053,613 A 4/2000 Wei et al.
6,069,698 A 5/2000 Ozawa et al.
6,078,047 A 6/2000 Mittleman et al.
6,091,496 A 7/2000 Hill
6,091,984 A 7/2000 Perelman et al.
6,094,274 A 7/2000 Yokoi
6,107,048 A 8/2000 Goldenring et al.
6,111,645 A 8/2000 Tearney et al.
6,117,128 A 9/2000 Gregory
6,120,516 A 9/2000 Selmon et al.
6,134,003 A 10/2000 Tearney et al.
6,134,010 A 10/2000 Zavislan
6,134,033 A 10/2000 Bergano et al.
6,141,577 A 10/2000 Rolland et al.
6,151,522 A 11/2000 Alfano et al.
6,159,445 A 12/2000 Klaveness et al.
6,160,826 A 12/2000 Swanson et al.
6,161,031 A 12/2000 Hochman et al.
6,166,373 A 12/2000 Mao
6,174,291 B1 1/2001 McMahon et al.
6,175,669 B1 1/2001 Colston et al.
6,185,271 B1 2/2001 Kinsinger
6,191,862 B1 2/2001 Swanson et al.
6,193,676 B1 2/2001 Winston et al.
6,198,956 B1 3/2001 Dunne
6,201,989 B1 3/2001 Whitehead et al.
6,208,415 B1 3/2001 De Boer et al.
6,208,887 B1 3/2001 Clarke
6,245,026 B1 6/2001 Campbell et al.
6,249,349 B1 6/2001 Lauer
6,249,381 B1 6/2001 Suganuma
6,249,630 B1 6/2001 Stock et al.
6,263,234 B1 7/2001 Engelhardt et al.
6,264,610 B1 7/2001 Zhu
6,272,268 B1 8/2001 Miller et al.
6,272,376 B1 8/2001 Marcu et al.
6,274,871 B1 8/2001 Dukor et al.
6,282,011 B1 8/2001 Tearney et al.
6,297,018 B1 10/2001 French et al.
6,301,048 B1 10/2001 Cao et al.
6,308,092 B1 10/2001 Hoyns
6,324,419 B1 11/2001 Guzelsu et al.
6,341,036 B1 1/2002 Tearney et al.
6,353,693 B1 3/2002 Kano et al.
6,359,692 B1 3/2002 Groot
6,374,128 B1 4/2002 Toida et al.
6,377,349 B1 4/2002 Fercher
6,384,915 B1 5/2002 Everett et al.
6,393,312 B1 5/2002 Hoyns
6,394,964 B1 5/2002 Sievert, Jr. et al.
6,396,941 B1 5/2002 Bacus et al.
6,421,164 B2 7/2002 Tearney et al.
6,437,867 B2 8/2002 Zeylikovich et al.
6,441,892 B2 8/2002 Xiao et al.
6,441,959 B1 8/2002 Yang et al.
6,445,485 B1 9/2002 Frigo et al.
6,445,939 B1 9/2002 Swanson et al.
6,445,944 B1 9/2002 Ostrovsky
6,459,487 B1 10/2002 Chen et al.
6,463,313 B1 10/2002 Winston et al.
6,469,846 B2 10/2002 Ebizuka et al.
6,475,159 B1 11/2002 Casscells et al.
6,475,210 B1 11/2002 Phelps et al.
6,477,403 B1 11/2002 Eguchi et al.
6,485,413 B1 * 11/2002 Boppart et al. ..... 600/160
6,485,482 B1 11/2002 Belef
6,501,551 B1 12/2002 Tearney et al.
6,501,878 B2 12/2002 Hughes et al.
6,516,014 B1 2/2003 Sellin et al.
6,517,532 B1 2/2003 Altshuler et al.
6,538,817 B1 3/2003 Farmer et al.
6,540,391 B2 4/2003 Lanzetta et al.
6,549,801 B1 4/2003 Chen et al.
6,552,796 B2 4/2003 Magnin et al.
6,556,305 B1 4/2003 Aziz et al.
6,556,853 B1 4/2003 Cabib et al.
6,558,324 B1 5/2003 Von Behren et al.
6,560,259 B1 5/2003 Hwang et al.
6,564,087 B1 5/2003 Pitris et al.
6,564,089 B2 5/2003 Izatt et al.
6,567,585 B2 5/2003 Harris
6,593,101 B2 7/2003 Richards-Kortum et al.
6,611,833 B1 8/2003 Johnson
6,615,071 B1 9/2003 Casscells, III et al.
6,622,732 B2 9/2003 Constantz
6,654,127 B2 11/2003 Everett et al.
6,657,730 B2 12/2003 Pfau et al.
6,658,278 B2 12/2003 Gruhl
6,680,780 B1 1/2004 Fee
6,685,885 B2 2/2004 Nolte et al.
6,687,007 B1 2/2004 Meigs
6,687,010 B1 2/2004 Horii et al.
6,687,036 B2 2/2004 Riza
6,692,430 B2 2/2004 Adler
6,701,181 B2 3/2004 Tang et al.
6,721,094 B1 4/2004 Sinclair et al.
6,725,073 B1 4/2004 Motamedi et al.
6,738,144 B1 5/2004 Dogariu et al.
6,741,355 B2 5/2004 Drabarek

(56) References Cited

U.S. PATENT DOCUMENTS 6,741,884 B1 5/2004 Freeman et al.
6,757,467 B1 6/2004 Rogers
6,790,175 B1 9/2004 Furusawa et al.
6,806,963 B1 10/2004 Wälti et al.
6,816,743 B2 11/2004 Moreno et al.
6,831,781 B2 12/2004 Tearney et al.
6,839,496 B1 1/2005 Mills et al.
6,882,432 B2 4/2005 Deck
6,900,899 B2 5/2005 Nevis
6,903,820 B2 6/2005 Wang
6,909,105 B1 6/2005 Heintzmann et al.
6,949,072 B2 9/2005 Furnish et al.
6,961,123 B1 11/2005 Wang et al.
6,980,299 B1 12/2005 de Boer
6,996,549 B2 2/2006 Zhang et al.
7,006,231 B2 2/2006 Ostrovsky et al.
7,006,232 B2 2/2006 Rollins et al.
7,019,838 B2 3/2006 Izatt et al.
7,027,633 B2 4/2006 Foran et al.
7,061,622 B2 6/2006 Rollins et al.
7,072,047 B2 7/2006 Westphal et al.
7,075,658 B2 7/2006 Izatt et al.
7,099,358 B1 8/2006 Chong
7,113,288 B2 9/2006 Fercher
7,113,625 B2 9/2006 Watson et al.
7,130,320 B2 10/2006 Tobiason et al.
7,139,598 B2 11/2006 Hull et al.
7,142,835 B2 11/2006 Paulus
7,148,970 B2 12/2006 De Boer
7,177,027 B2 2/2007 Hirasawa et al.
7,190,464 B2 3/2007 Alphonse
7,230,708 B2 6/2007 Lapotko et al.
7,231,243 B2 6/2007 Tearney et al.
7,236,637 B2 6/2007 Sirohey et al.
7,242,480 B2 7/2007 Alphonse
7,267,494 B2 9/2007 Deng et al.
7,272,252 B2 9/2007 De La Torre-Bueno et al.
7,304,798 B2 12/2007 Izumi et al.
7,310,150 B2 12/2007 Guillermo et al.
7,330,270 B2 2/2008 O'Hara et al.
7,336,366 B2 2/2008 Choma et al.
7,342,659 B2 3/2008 Horn et al.
7,355,716 B2 4/2008 De Boer et al.
7,355,721 B2 4/2008 Quadling et al.
7,359,062 B2 4/2008 Chen et al.
7,365,858 B2 4/2008 Fang-Yen et al.
7,366,376 B2 4/2008 Shishkov et al.
7,382,809 B2 6/2008 Chong et al.
7,391,520 B2 6/2008 Zhou et al.
7,458,683 B2 12/2008 Chernyak
7,530,948 B2 5/2009 Seibel et al.
7,539,530 B2 5/2009 Caplan et al.
7,609,391 B2 10/2009 Betzig
7,630,083 B2 12/2009 de Boer et al.
7,643,152 B2 1/2010 de Boer et al.
7,643,153 B2 1/2010 de Boer et al.
7,646,905 B2 1/2010 Guittet et al.
7,649,160 B2 1/2010 Colomb et al.
7,664,300 B2 2/2010 Lange et al.
7,733,497 B2 6/2010 Yun et al.
7,782,464 B2 8/2010 Mujat et al.
7,799,558 B1 9/2010 Dultz
7,805,034 B2 9/2010 Kato et al.
7,911,621 B2 3/2011 Motaghiannezam et al.
7,969,578 B2 6/2011 Yun et al.
7,973,936 B2 7/2011 Dantus
8,315,282 B2 11/2012 Huber et al.
2001/0020126 A1 9/2001 Swanson et al.
2001/0036002 A1 11/2001 Tearney et al.
2001/0047137 A1 11/2001 Moreno et al.
2001/0055462 A1 12/2001 Seibel
2002/0016533 A1 2/2002 Marchitto et al.
2002/0024015 A1 2/2002 Hoffmann et al.
2002/0037252 A1 3/2002 Toida et al.
2002/0048025 A1 4/2002 Takaoka
2002/0048026 A1 4/2002 Isshiki et al.
2002/0052547 A1 5/2002 Toida
2002/0057431 A1 5/2002 Fateley et al.
2002/0064341 A1 5/2002 Fauver et al.
2002/0076152 A1 6/2002 Hughes et al.
2002/0085209 A1 7/2002 Mittleman et al.
2002/0086347 A1 7/2002 Johnson et al.
2002/0091322 A1 7/2002 Chaiken et al.
2002/0093662 A1 7/2002 Chen et al.
2002/0109851 A1 8/2002 Deck
2002/0113965 A1 8/2002 Roche et al.
2002/0122182 A1 9/2002 Everett et al.
2002/0122246 A1 9/2002 Tearney et al.
2002/0140942 A1 10/2002 Fee et al.
2002/0158211 A1 10/2002 Gillispie
2002/0161357 A1 10/2002 Anderson et al.
2002/0163622 A1 11/2002 Magnin et al.
2002/0166946 A1 11/2002 Iizuka et al.
2002/0168158 A1 11/2002 Furusawa et al.
2002/0172485 A1 11/2002 Keaton et al.
2002/0183623 A1 12/2002 Tang et al.
2002/0188204 A1 12/2002 McNamara et al.
2002/0196446 A1 12/2002 Roth et al.
2002/0198457 A1 12/2002 Tearney et al.
2003/0001071 A1 1/2003 Mandella et al.
2003/0013973 A1 1/2003 Georgakoudi et al.
2003/0023153 A1 1/2003 Izatt et al.
2003/0025917 A1 2/2003 Suhami
2003/0026735 A1 2/2003 Nolte et al.
2003/0028114 A1 2/2003 Casscells, III et al.
2003/0030816 A1 2/2003 Eom et al.
2003/0043381 A1 3/2003 Fercher
2003/0053673 A1 3/2003 Dewaele et al.
2003/0067607 A1 4/2003 Wolleschensky et al.
2003/0082105 A1 5/2003 Fischman et al.
2003/0097048 A1 5/2003 Ryan et al.
2003/0103212 A1 6/2003 Westphal et al.
2003/0108911 A1 6/2003 Klimant et al.
2003/0120137 A1 6/2003 Pawluczyk et al.
2003/0135101 A1 7/2003 Webler
2003/0137669 A1 7/2003 Rollins et al.
2003/0164952 A1 9/2003 Deichmann et al.
2003/0165263 A1 9/2003 Hamer et al.
2003/0171691 A1 9/2003 Casscells, III et al.
2003/0174339 A1 9/2003 Feldchtein et al.
2003/0191392 A1 10/2003 Haldeman
2003/0199769 A1 10/2003 Podoleanu et al.
2003/0216719 A1 11/2003 Debenedictis et al.
2003/0218756 A1 11/2003 Chen et al.
2003/0220749 A1 11/2003 Chen et al.
2003/0236443 A1 12/2003 Cespedes et al.
2004/0002650 A1 1/2004 Mandrusov et al.
2004/0039252 A1 2/2004 Koch
2004/0039298 A1 2/2004 Abreu
2004/0054268 A1 3/2004 Esenaliev et al.
2004/0072200 A1 4/2004 Rigler et al.
2004/0075841 A1 4/2004 Van Neste et al.
2004/0076940 A1 4/2004 Alexander et al.
2004/0077949 A1 4/2004 Blofgett et al.
2004/0085540 A1 5/2004 Lapotko et al.
2004/0086245 A1 5/2004 Farroni et al.
2004/0095464 A1 5/2004 Miyagi et al.
2004/0100631 A1 5/2004 Bashkansky et al.
2004/0100681 A1 5/2004 Bjarklev et al.
2004/0110206 A1 6/2004 Wong et al.
2004/0126048 A1 7/2004 Dave et al.
2004/0126120 A1 7/2004 Cohen et al.
2004/0133191 A1 7/2004 Momiuchi et al.
2004/0150829 A1 8/2004 Koch et al.
2004/0150830 A1 8/2004 Chan
2004/0152989 A1 8/2004 Puttappa et al.
2004/0165184 A1 8/2004 Mizuno
2004/0166593 A1 8/2004 Nolte et al.
2004/0188148 A1 9/2004 Chen et al.
2004/0189999 A1 9/2004 De Groot et al.
2004/0204651 A1 10/2004 Freeman et al.
2004/0212808 A1 10/2004 Okawa et al.
2004/0239938 A1* 12/2004 Izatt ..... 356/450
2004/0246490 A1 12/2004 Wang

(56) References Cited

U.S. PATENT DOCUMENTS

2004/0246583 A1 12/2004 Mueller et al.
2004/0247268 A1 12/2004 Ishihara et al.
2004/0254474 A1 12/2004 Seibel et al.
2004/0258106 A1 12/2004 Araujo et al.
2004/0263843 A1 12/2004 Knopp et al.
2005/0004453 A1 1/2005 Tearney et al.
2005/0018133 A1 1/2005 Huang et al.
2005/0018200 A1 1/2005 Guillermo et al.
2005/0018201 A1 1/2005 De Boer et al.
2005/0035295 A1 2/2005 Bouma et al.
2005/0036150 A1 2/2005 Izatt et al.
2005/0046837 A1 3/2005 Izumi et al.
2005/0049488 A1 3/2005 Homan
2005/0057680 A1 3/2005 Agan
2005/0057756 A1 3/2005 Fang-Yen et al.
2005/0059894 A1 3/2005 Zeng et al.
2005/0065421 A1 3/2005 Burckhardt et al.
2005/0075547 A1 4/2005 Wang
2005/0083534 A1 4/2005 Riza et al.
2005/0119567 A1 6/2005 Choi
2005/0128488 A1 6/2005 Yelin et al.
2005/0165303 A1 7/2005 Kleen et al.
2005/0171438 A1 8/2005 Chen et al.
2005/0190372 A1 9/2005 Dogariu et al.
2005/0197530 A1 9/2005 Wallace et al.
2005/0221270 A1 10/2005 Connelly et al.
2005/0254059 A1 11/2005 Alphonse
2005/0254061 A1 11/2005 Alphonse et al.
2006/0020172 A1 1/2006 Luerssen et al.
2006/0033923 A1 2/2006 Hirasawa et al.
2006/0039004 A1 2/2006 De Boer et al.
2006/0093276 A1 5/2006 Bouma et al.
2006/0103850 A1 5/2006 Alphonse et al.
2006/0106375 A1 5/2006 Werneth et al.
2006/0146339 A1 7/2006 Fujita et al.
2006/0155193 A1 7/2006 Leonardi et al.
2006/0164639 A1 7/2006 Horn et al.
2006/0167363 A1 7/2006 Bernstein et al.
2006/0171503 A1 8/2006 O'Hara et al.
2006/0184048 A1 8/2006 Saadat
2006/0189928 A1 8/2006 Camus et al.
2006/0193352 A1 8/2006 Chong et al.
2006/0224053 A1 10/2006 Black et al.
2006/0244973 A1 11/2006 Yun et al.
2006/0279742 A1 12/2006 Tearney
2007/0002435 A1 1/2007 Ye et al.
2007/0019208 A1 1/2007 Toida et al.
2007/0024860 A1 2/2007 Tobiason et al.
2007/0035743 A1 2/2007 Vakoc et al.
2007/0038040 A1 2/2007 Cense et al.
2007/0048818 A1 3/2007 Rosen et al.
2007/0070496 A1 3/2007 Gweon et al.
2007/0076217 A1 4/2007 Baker et al.
2007/0086013 A1 4/2007 De Lega et al.
2007/0086017 A1 4/2007 Buckland et al.
2007/0091317 A1 4/2007 Freischlad et al.
2007/0133002 A1* 6/2007 Wax et al. ..... 356/456
2007/0188855 A1 8/2007 Shishkov et al.
2007/0203404 A1 8/2007 Zysk et al.
2007/0208225 A1 9/2007 Czaniera et al.
2007/0223006 A1 9/2007 Tearney et al.
2007/0233056 A1 10/2007 Yun
2007/0233396 A1 10/2007 Tearney et al.
2007/0236700 A1 10/2007 Yun et al.
2007/0253901 A1 11/2007 Deng et al.
2007/0258094 A1 11/2007 Izatt et al.
2007/0263226 A1 11/2007 Kurtz et al.
2007/0291277 A1 12/2007 Everett et al.
2008/0002197 A1 1/2008 Sun et al.
2008/0007734 A1 1/2008 Park et al.
2008/0013960 A1 1/2008 Tearney et al.
2008/0021275 A1 1/2008 Tearney et al.
2008/0049220 A1 2/2008 Izzia et al.
2008/0070323 A1 3/2008 Hess et al.
2008/0094613 A1 4/2008 de Boer et al.
2008/0094637 A1 4/2008 de Boer et al.
2008/0097225 A1 4/2008 Tearney et al.
2008/0097709 A1 4/2008 de Boer et al.
2008/0100837 A1 5/2008 de Boer et al.
2008/0139906 A1 6/2008 Bussek et al.
2008/0152353 A1 6/2008 de Boer et al.
2008/0154090 A1 6/2008 Hashimshony
2008/0192236 A1 8/2008 Smith et al.
2008/0201081 A1 8/2008 Reid
2008/0204762 A1 8/2008 Izatt et al.
2008/0218696 A1 9/2008 Mir
2008/0226029 A1 9/2008 Weir et al.
2008/0228086 A1 9/2008 Ilegbusi
2008/0234560 A1 9/2008 Nomoto et al.
2008/0252901 A1 10/2008 Shimizu
2008/0265130 A1 10/2008 Colomb et al.
2008/0297806 A1 12/2008 Motaghiannezam
2008/0308730 A1 12/2008 Vizi et al.
2009/0004453 A1 1/2009 Murai et al.
2009/0005691 A1 1/2009 Huang
2009/0011948 A1 1/2009 Uniu et al.
2009/0012368 A1 1/2009 Banik et al.
2009/0044799 A1 2/2009 Bangsaruntip et al.
2009/0051923 A1 2/2009 Zuluaga
2009/0131801 A1 5/2009 Suter et al.
2009/0192358 A1 7/2009 Jaffer et al.
2009/0196477 A1 8/2009 Cense et al.
2009/0209834 A1 8/2009 Fine
2009/0273777 A1 11/2009 Yun et al.
2009/0281390 A1 11/2009 Qiunjun et al.
2009/0290156 A1 11/2009 Popescu et al.
2009/0305309 A1 12/2009 Chien et al.
2009/0306520 A1 12/2009 Schmitt et al.
2009/0323056 A1 12/2009 Yun et al.
2010/0002241 A1 1/2010 Hirose
2010/0086251 A1 4/2010 Xu et al.
2010/0094576 A1 4/2010 de Boer et al.
2010/0145145 A1 6/2010 Shi et al.
2010/0150467 A1 6/2010 Zhao et al.
2010/0261995 A1 10/2010 Mckenna et al.
2010/0309477 A1 12/2010 Yun et al.
2011/0028967 A1 2/2011 Rollins et al.
2011/0160681 A1 6/2011 Dacey, Jr. et al.
2011/0218403 A1 9/2011 Tearney et al.

FOREIGN PATENT DOCUMENTS

DE 102005034443 2/2007
EM 0617286 2/1994
EM 1324051 7/2003
EP 0110201 6/1984
EP 0617286 2/1994
EP 0590268 4/1994
EP 0697611 2/1996
EP 0728440 8/1996
EP 0251062 1/1998
EP 0933096 8/1999
EP 1324051 6/2003
EP 1324051 7/2003
EP 1426799 6/2004
EP 2149776 2/2010
FR 2738343 8/1995
GB 1257778 12/1971
GB 2030313 4/1980
GB 2209221 5/1989
GB 2298054 8/1996
JP 6073405 4/1985
JP 361040633 3/1986
JP 62-188001 6/1989
JP 04-056907 2/1992
JP 2004056907 2/1992
JP 4135550 5/1992
JP 4135551 5/1992
JP 5509417 11/1993
JP H8-136345 5/1996
JP H08-160129 6/1996
JP 9-10213 1/1997
JP 9-230248 9/1997
JP 10-213485 8/1998

(56) References Cited

FOREIGN PATENT DOCUMENTS

| | | |
|---|---|---|
| JP | 10-267631 | 10/1998 |
| JP | 10-267830 | 10/1998 |
| JP | 2259617 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000-126116 | 5/2000 |
| JP | 2000-131222 | 5/2000 |
| JP | 2001-4447 | 1/2001 |
| JP | 2001-500026 | 1/2001 |
| JP | 2001-104315 | 4/2001 |
| JP | 2001-174404 | 6/2001 |
| JP | 2001-174744 | 6/2001 |
| JP | 2001-507251 | 6/2001 |
| JP | 2001-508340 | 6/2001 |
| JP | 2007-539336 | 6/2001 |
| JP | 2001-212086 | 8/2001 |
| JP | 2008-533712 | 8/2001 |
| JP | 2001-264246 | 9/2001 |
| JP | 2001-515382 | 9/2001 |
| JP | 2001-525580 | 12/2001 |
| JP | 2002-503134 | 1/2002 |
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214127 | 7/2002 |
| JP | 2002-214128 | 7/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-089552 | 3/2004 |
| JP | 2004-113780 | 4/2004 |
| JP | 2004-514920 | 5/2004 |
| JP | 2004-258144 | 9/2004 |
| JP | 2004-317437 | 11/2004 |
| JP | 2005-062850 | 3/2005 |
| JP | 2005-110208 | 4/2005 |
| JP | 2005-510323 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-237359 | 9/2006 |
| JP | 2007-500059 | 1/2007 |
| JP | 2007-075403 | 3/2007 |
| JP | 2007-83053 | 4/2007 |
| JP | 2007-524455 | 8/2007 |
| JP | 2007271761 | 10/2007 |
| JP | 2003-102672 | 4/2012 |
| RU | 2149464 | 5/2000 |
| RU | 2209094 | 7/2003 |
| RU | 2213421 | 9/2003 |
| RU | 2242710 | 12/2004 |
| RU | 2255426 | 6/2005 |
| RU | 2108122 | 6/2006 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 96-02184 | 2/1996 |
| WO | 96-04839 | 2/1996 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 98-35203 | 8/1998 |
| WO | 9838907 | 9/1998 |
| WO | 9846123 | 10/1998 |
| WO | 9848838 | 11/1998 |
| WO | 9848846 | 11/1998 |
| WO | 9905487 | 2/1999 |
| WO | 9944089 | 2/1999 |
| WO | 99-28856 | 6/1999 |
| WO | 99-45838 | 9/1999 |
| WO | 9944089 | 9/1999 |
| WO | 99-45338 | 10/1999 |
| WO | 9957507 | 11/1999 |
| WO | 00-42906 | 7/2000 |
| WO | 00-43730 | 7/2000 |
| WO | 0058766 | 10/2000 |
| WO | 01-04828 | 1/2001 |
| WO | 0101111 | 1/2001 |
| WO | 0108579 | 2/2001 |
| WO | 0127679 | 4/2001 |
| WO | 01-33215 | 5/2001 |
| WO | 01-38820 | 5/2001 |
| WO | 01-42735 | 6/2001 |
| WO | 01-82786 | 11/2001 |
| WO | 02-37075 | 5/2002 |
| WO | 0236015 | 5/2002 |
| WO | 0238040 | 5/2002 |
| WO | 02037075 | 5/2002 |
| WO | 02-45572 | 6/2002 |
| WO | 02-68853 | 6/2002 |
| WO | 02-054027 | 7/2002 |
| WO | 02053050 | 7/2002 |
| WO | 02-083003 | 10/2002 |
| WO | 02084263 | 10/2002 |
| WO | 03-003903 | 1/2003 |
| WO | 03-012405 | 2/2003 |
| WO | 03-013624 | 2/2003 |
| WO | 03013624 | 2/2003 |
| WO | 03020119 | 3/2003 |
| WO | 03046495 | 6/2003 |
| WO | 03046636 | 6/2003 |
| WO | 03052478 | 6/2003 |
| WO | 03053226 | 7/2003 |
| WO | 03062802 | 7/2003 |
| WO | 03-088826 | 10/2003 |
| WO | 03105678 | 12/2003 |
| WO | 2004034569 | 4/2004 |
| WO | 2004-037068 | 5/2004 |
| WO | 2004-043251 | 5/2004 |
| WO | 2004057266 | 7/2004 |
| WO | 2004066824 | 8/2004 |
| WO | 2004-073501 | 9/2004 |
| WO | 2004088361 | 10/2004 |
| WO | 2004-100789 | 11/2004 |
| WO | 2004-105598 | 12/2004 |
| WO | 2005000115 | 1/2005 |
| WO | 2005-045362 | 5/2005 |
| WO | 2005-047813 | 5/2005 |
| WO | 2005047813 | 5/2005 |
| WO | 2005054780 | 6/2005 |
| WO | 2005082225 | 9/2005 |
| WO | 20050082225 | 9/2005 |
| WO | 2006004743 | 1/2006 |
| WO | 2006-020605 | 2/2006 |
| WO | 2006014392 | 2/2006 |
| WO | 2006039091 | 4/2006 |
| WO | 20060038876 | 4/2006 |
| WO | 2006-050320 | 5/2006 |
| WO | 2006-058187 | 6/2006 |
| WO | 2006059109 | 6/2006 |
| WO | 2006124860 | 11/2006 |
| WO | 2006-131859 | 12/2006 |
| WO | 2006130797 | 12/2006 |
| WO | 2007-030835 | 3/2007 |
| WO | 2007028531 | 3/2007 |

(56) References Cited

FOREIGN PATENT DOCUMENTS

| | | |
|---|---|---|
| WO | 2007038787 | 4/2007 |
| WO | 2007083138 | 7/2007 |
| WO | 2007084995 | 7/2007 |
| WO | 2009-033064 | 3/2009 |
| WO | 20090153929 | 12/2009 |
| WO | 2011-055376 | 5/2011 |
| WO | 2011-080713 | 7/2011 |

OTHER PUBLICATIONS

Choma et al. ["Sensitivity advantage of swept source and Fourier domain optical coherence tomography"] published by Optics Express, vol. 11, No. 18, Sep. 8, 2003, pp. 2183-2189.*
The Office Action for Chinese Patent Application No. 200780010517.7 mailed on Apr. 6, 2016.
K.M. Yung et al. "Phase-Domain Processing of Optical Coherence Tomography Images" J. of Biomedical Optics 4(1) pp. 125-136, Jan. 1999.
The Office Action for Japanese Patent Application No. 2013-205046 mailed on Jan. 6, 2015.
Pyhtila, Optics Express, U.S.A., Optical Society of America, Dec. 13, 2004, V12 N25.
Office Action dated Oct. 1, 2008 for U.S. Appl. No. 11/955,986.
Invitation to Pay Additional Fees dated Aug. 7, 2008 for International Application No. PCT/US2008/062354.
Invitation to Pay Additional Fees dated Jul. 29, 2008 for International Application No. PCT/US2007/081982.
International Search Report and Written Opinion dated Mar. 7, 2006 for International Search Report for PCT/US2005/035711.
International Search Report and Written Opinion dated Jul. 18, 2008 for International Application No. PCT/US2008/05733.
International Search Report and Written Opinion date Jul. 4, 2008 for International Application No. PCT/US2008/051432.
Australian Examiner's Report dated May 27, 2008 for Australian Patent Application No. 2003210669.
International Search Report and Written Opinion dated Jun. 10, 2008 for International Application No. PCT/US2008/051335.
Office Action dated Aug. 25, 2008 for U.S. Appl. No. 09/709,162.
International Search Report and Written Opinion dated Oct. 9, 2008 for International Application No. PCT/US2008/081982.
International Search Report and Written Opinion dated Aug. 27, 2008 for International Application No. PCT/US2008/060600.
International Search Report and Written Opinion dated Aug. 7, 2008 for International Application No. PCT/US2007/074873.
International Search Report and Written Opinion dated Feb. 5, 2007 for International Application No. PCT/US2006/031275.
International Search Report and Written Opinion dated Mar. 23, 2006 for International Application No. PCT/US2005/042408.
Japanese Office Action dated Dec. 2, 2008.
European Official Communication dated Feb. 12, 2008 for EP 07718117.0.
International Search Report and Written Opinion dated Jun. 10, 2009 for PCT/US2008/075456.
Notice of Reasons for Reject dated Jul. 14, 2009 for Japanese Application No. 2006-503161.
International Search Report and Written Opinion dated Dec. 23, 2009.
Office Action dated Jan. 9, 2009 for U.S. Appl. No. 11/624,455.
Office Action dated Mar. 24, 2009 for U.S. Appl. No. 11/744,412.
Summons to attend Oral Proceedings for European Patent No. 06813365.1 dated Oct. 9, 2009.
Office Action dated Dec. 14, 2009 for U.S. Appl. No. 11/537,123.
Office Action dated May 28, 2010 for U.S. Appl. No. 12/015,642.
Office Action dated Jun. 2, 2010 for U.S. Appl. No. 12/112,205.
European Search Report dated Dec. 3, 2010 for EP 10182442.3.
Notice of Reasons for Rejection dated May 5, 2010 for JP 2006-515266.
Office Action dated Jun. 4, 2010 for U.S. Appl. No. 11/285,301.
Office Action dated Jun. 8, 2010 for U.S. Appl. No. 12/201,816.
Chinese Office Action dated Jun. 8, 2010 for Chinese application No. 200780031332.4.
Office Action dated Jun. 10, 2010 for U.S. Appl. No. 11/505,700.
European Office Action dated Jun. 11, 2010 for EP 07761877.5.
European Office Action dated Jul. 14, 2010 for EP 06751266.5.
Office Action dated Sep. 29, 2010 for U.S. Appl. No. 11/672,571.
International Search Report and Written Opinion dated Aug. 31, 2010 for PCT/US2010/022034.
Office Action dated Oct. 20, 2010 for U.S. Appl. No. 12/015,642.
Office Action dated Oct. 25, 2010 for U.S. Appl. No. 11/622,854.
Office Action dated Oct. 26, 2010 for U.S. Appl. No. 11/211,482.
Office Action dated Oct. 27, 2010 for U.S. Appl. No. 11/744,287.
Office Action dated Nov. 15, 2010 for U.S. Appl. No. 12/795,529.
Notice of Allowance and Fees mailed Nov. 23, 2010 for U.S. Appl. No. 12/627,918.
Office Action dated Nov. 24, 2010 for U.S. Appl. No. 11/624,334.
Notice of Allowance and Fees mailed Dec. 1, 2010 for U.S. Appl. No. 12/261,967.
Office Action mailed Dec. 3, 2010 for U.S. Appl. No. 12/210,979.
International Search Report and Written Opinion dated Feb. 23, 2011 for PCT/US2010/041923.
Extended European Search Report mailed Dec. 14, 2010 for EP 10182301.1.
International Search report dated Apr. 29, 2011 for PCT/US2010/051715.
International Search report dated Sep. 13, 2010 for PCT/US2010/023215.
International Search report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).

(56) References Cited

OTHER PUBLICATIONS

E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesocopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
Notice of Reasons for Rejection dated Nov. 2, 2011 for JP 2008-509233.
Notice of Reasons for Rejection dated Nov. 21, 2011 for JP 2007-525075.
Extended European Search Report dated Nov. 28, 2011 for EP 09767845.2.
International Search Report and Written Opinion for PCT/US2011/037916 mailed Dec. 27, 2011.
International Search Report and Written Opinion for PCT/US2011/039066 mailed Dec. 28, 2011.
Communication pursuant to Article 94(3) for EP 10186189.6 mailed Dec. 22, 2011.
International Search Report and Written Opinion for PCT/US2011/038421 mailed Jan. 12, 2012.
Japanese Language Appeal Decision mailed Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP2003516531.
International Search Report and Written Opinion mailed Feb. 9, 2012 based on PCT/US2011/034810.
European Search Report dated Mar. 2, 2012 for EP 11188120.7.
Japanese Notice of Reasons for Rejection dated Feb. 17, 2012 for JP 2007-539336.
(Japanese Notice of Reasons for Rejection dated Feb. 15, 2012 for JP2008-553509.
Japanese Notice of Reasons for Rejection dated Mar. 27, 2012 for JP 2008-554495.
Japanese Notice of Reasons for Rejection dated May 8, 2012 for JP 2008-533727.
Korean Office Action dated May 25, 2012 for KR 10-2007-7008116.
International Search Report and Written Opinion dated May 29, 2012 for PCT/US2011/058110.
International Search Report and Written Opinion dated May 29, 2012 for PCT/US2011/05007.
Japanese Notice of Reasons for Rejection dated Mar. 13, 2012 for JP2009-063553.
Japanese Notice of Reasons for Rejection dated May 21, 2012 for JP 2008-551523.
Japanese Notice of Reasons for Rejection dated Jun. 20, 2012 for JP 2009-546534.
Japanese Notice of Reasons for Rejection dated Jun. 26, 2012 for JP 2002-585939.
European Official Action dated Aug. 1, 2012 for EP 10193526.0.
European Search Report dated Jun. 25, 2012 for EP 10733985.5.
European Communication Pursuant to EPC Article 94(3) for EP 07845206.7 dated Aug. 30, 2012.
International Search Report and Written Opinion mailed Aug. 30, 2012 for PCT/US2012/035234.
International Search Report and Written Opinion mailed on Aug. 16, 2012 for PCT/US2012/035887.
Japanese Notice of Reasons for Rejections dated Oct. 10, 2012 for 2008-553511.
Japanese Notice of Reasons for Rejections dated Oct. 2, 2012 for 2007-543626.
Canadian Office Action dated Oct. 10, 2012 for 2,514,189.
Japanese Notice of Reasons for Rejections dated Nov. 9, 2012 for 2007-530134.
Japanese Notice of Reasons for Rejection dated Nov. 27, 2012 for 2009-554772.
Japanese Notice of Reasons for Rejection dated Oct. 11, 2012 for 2008-533712.
Japanese Notice of Reasons for Rejection dated Dec. 18, 2012 for 2011-136398.
International Search Report and Written Opinion mailed Oct. 25, 2012 for PCT/US2012/047415.
International Search Report and Written Opinion mailed on Aug. 16, 2012 for PCT/US2012/051132.
European Official Communication mailed on Feb. 11, 2013 for EP 08837490.5.
European Official Communication mailed on Feb. 15, 2012 for EP 04822169.1.
International Search Report mailed Jan. 31, 2013 for PCT/US2012/061135.
International Search Report and Written Opinion mailed Jan. 31, 2013 for PCT/US2012/060843.
European Search Report mailed on Mar. 11, 2013 for EP 10739129.4.
Notice of Reasons for Rejection dated Feb. 5, 2013 for JP 2008-509233.
Notice of Reasons for Rejection dated Feb. 19, 2013 for JP 2008-507983.
European Extended Search Report mailed Mar. 26, 2013 for EP 09825421.1.
International Search Report and Written Opinion mailed on Dec. 6, 2012 for PCT/US2012/052553.
European Extended Search Report mailed on Feb. 1, 2013 for EP 12171521.3.
Official European Search report mailed on Apr. 24, 2013 for EP 10182341.7.
Notice of Reasons for Rejection mailed on Apr. 16, 2013 for JP 2008-533727.
Notice of Reasons for Rejection mailed on Apr. 16, 2013 for JP 2009-510092.
Notice of Reasons for Rejection mailed on May 7, 2013 for JP 2011-508674.
European Search Report for 12194876.4 dated Feb. 1, 2013.
Japanese Notice of Reasons for Rejection for 2010-529142 dated Jan. 29, 2013.

(56) References Cited

OTHER PUBLICATIONS

Japanese Notice of Reasons for Rejection for 2007-539336 dated May 21, 2013.
International Search Report and Written Opinion for PCT/US2013/022136.
European Official Communication dated Jun. 28, 2013 for EP 09158713.9.
Japanese Notice of Reasons for Rejection for 2013-026897 dated Jun. 6, 2013.
Japanese Notice of Reasons for Rejection for 2013-026880 dated Jun. 6, 2013.
International Application Search Report and Written Opinion dated Apr. 11, 2013 for PCT/US2013/021299.
Extended European Search Report dated Jul. 2, 2013 for EP 10738929.8.
European Search Report dated Jul. 15, 2013 for EP 10800455.7.
European Search Report dated Jul. 26, 2013 for EP 09743687.7.
Extended European Search Report dated Jul. 11, 2013 for EP 09832543.4.
Japanese Office Action dated Aug. 20, 2013 for JP 2011-546443.
International Search Report and Written Opinion dated Sep. 19, 2013 for PCT/US2013/042008.
Japanese Notice of Reasons for Rejection dated Jul. 16, 2013 for JP 2009-063553.
Korean Notification of Ground for Rejection dated Sep. 30, 2013 for 10-2007-7027721.
European Search Report dated Sep. 10, 2013 for EP 10183412.5.
Japanese Official Action dated Oct. 15, 2013 for JP 2012-181098.
Japanese Office Action dated Oct. 8, 2013 for JP 2011-168738.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Reasons for Rejection dated Dec. 12, 2011 for JP 2008-533712.
Japanese Notice of Reasons for Rejection dated Mar. 27, 2012 for JP 2003-102672.
European Official Communication dated Aug. 1, 2012 for EP 10193526.0.
Wieser, Wolfgang et al., "Multi-Megahertz OCT: High Quality 3D Imaging at 20 million A-Scans and 4.5 Gvoxels Per Second" Jul. 5, 2010, vol. 18, No. 14, Optics Express.
Giuliano, Scarcelli et al., "Three-Dimensional Brillouin Confocal Microscopy". Optical Society of American, 2007, CtuV5.
Giuliano, Scarcelli et al., "Confocal Brillouin Microscopy for Three-Dimensional Mechanical Imaging." Nat Photonis, Dec. 9, 2007.
W.Y. Oh et al: "High-Speed Polarization Sensitive Optical Frequency Domain Imaging with Frequency Multiplexing", Optics Express, vol. 16, No. 2, Jan. 1, 2008.
Athey, B.D. et al., "Development and Demonstration of a Networked Telepathology 3-D Imaging, Databasing, and Communication System", 1998 ("C2") , pp. 5-17.
D'Amico, A.V., et al., "Optical Coherence Tomography as a Method for Identifying Benign and Maliganat Microscopic Structures in the Prostate Gland", Urology, vol. 55, Isue 5, May 2000 ("C3"), pp. 783-787.
Tearney, G.J. et al., "In Vivo Endoscopic Optical Biopsy with Optical Coherence Tomography", Science, vol. 276, No. 5321, Jun. 27, 1997 ("C6"), pp. 2037-2039.
Japanese Notice of Reasons for Rejections dated Nov. 9, 2012 for JP 2007-530134.
Japanese Notice of Reasons for Rejections dated Nov. 27, 2012 for JP 2009-554772.
Japanese Notice of Reasons for Rejections dated Oct. 11, 2012 for JP 2008-533712.
Yoden, K. et al. "An Approach to Optical Reflection Tomography Along the Geometrial Thickness," Optical Review, vol. 7, No. 5, Oct. 1, 2000.
Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.
European Official Communication dated Feb. 6, 2013 for 04822169.1.
Viliyam K. Pratt. Lazernye Sistemy Svyazi. Moskva, Izdatelstvo "Svyaz", 1972. p. 68-70.
European Search Report mailed on Mar. 11, 2013 doe EP 10739129.4.
Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.
M. Kourogi et al: "Programmable High Speed (1MHz) Vernier-mode-locked Frequency-Swept Laser for OCT Imaging", Proceedings of SPIE, vol. 6847, Feb. 7, 2008.
Masahiro, Yamanari et al: "Polarization-Sensitive Swept-Source Optical Coherence Tomography with Continuous Source Polarization Modulation", Optics Express, vol. 16, No. 8, Apr. 14, 2008.
Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.
Lee, Seok-Jeong et al., "Ultrahigh Scanning Speed Optical Coherence Tomography Using Optical Frequency Comb Generators", The Japan Soceity of Applied Physics, vol. 40 (2001).
Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.
Bachmann A.H. et al: "Heterodyne Fourier Domain Optical Coherence Tomography for Full Range Probing with High Axial Resolution", Optics Express, OSA, vol. 14, No. 4, Feb. 20, 2006.
Thomas J. Flotte: "Pathology Correlations with Optical Biopsy Techniques", Annals of the New York Academy of Sciences, Wiley-Blackwell Publishing, Inc. SU, vol. 838, No. 1, Feb. 1, 1998, pp. 143-149.
Constance R. Chu et al: Arthroscopic Microscopy of Articular Cartilage Using Optical Coherence Tomography, American Journal of Sports Medicine, American Orthopedic Society for Sports Medicine, Waltham, MA, Vo. 32, No. 9, Apr. 1, 2004.
Bouma B E et al: Diagnosis of Specialized Intestinal Metaplasia of the Esophagus with Optical Coherence Tomography, Conference on Lasers and Electro-Optics. Technical Digest. OSA, US, vol. 56, May 6, 2001
Shen et al: "Ex Vivo Histology-Correlated Optical Coherence Tomography in the Detection of Transmural Inflammation in Crohn's Disease", Clinical Gastroenterology and Heptalogy, vol. 2, No. 9, Sep. 1, 2004.
Shen et al: "In Vivo Colonscopic Optical Coherence Tomography for Transmural Inflammation in Inflammatory Bowel Disease", Clinical Gastroenterology and Hepatology, American Gastroenterological Association, US, vol. 2, No. 12, Dec. 1, 2004.
Ge Z et al: "Identification of Colonic Dysplasia and Neoplasia by Diffuse Reflectance Spectroscopy and Pattern Recognition Techniques", Applied Spectroscopy, The Society for Applied Spectroscopy, vol. 52, No. 6, Jun. 1, 1998.
Elena Zagaynova et al: "Optical Coherence Tomography: Potentialities in Clinical Practice", Proceedings of SPIE, Aug. 20, 2004.
Westphal et al: "Correlation of Endoscopic Optical Coherence Tomography with Histology in the Lower-GI Tract", Gastrointestinal Endoscopy, Elsevier, NL, vol. 61, No. 4, Apr. 1, 2005.
Haggitt et al: "Barrett's Esophaagus, Dysplasia, and Adenocarcinoma", Human Pathology, Saunders, Philadelphia, PA, US, vol. 25, No. 10, Oct. 1, 1994.
Gang Yao et al. "Monte Carlo Simulation of an Optical Coherence Tomography Signal in Homogenous Turbid Media," Physics in Medicine and Biology, 1999.

(56) References Cited

OTHER PUBLICATIONS

Murakami, K. "A Miniature Confocal Optical Scanning Microscopy for Endscopes", Proceedings of SPIE, vol. 5721, Feb. 28, 2005, pp. 119-131.
Seok, H. Yun et al: "Comprehensive Volumetric Optical Microscopy in Vivo", Nature Medicine, vol. 12, No. 12, Jan. 1, 2007.
Baxter: "Image Zooming", Jan. 25, 2005, Retrieved from the Internet.
Qiang Zhou et al: "A Novel Machine Vision Application for Analysis and Visualization of Confocal Microscopic Images" Machine Vision and Applications, vol. 16, No. 2, Feb. 1, 2005.
Igor Gurov et al: (2007) "Full-field High-Speed Optical Coherence Tomography System for Evaluting Multilayer and Random Tissues", Proc. Of SPIE, vol. 6618.
Igor Gurov et al: "High-Speed Signal Evaluation in Optical Coherence Tomography Based on Sub-Nyquist Sampling and Kalman Filtering Method" AIP Coherence Proceedings, vol. 860, Jan. 1, 2006.
Groot De P et al: "Three Dimensional Imaging by Sub-Nyquist Sampling of White-Light Interferograms", Optics Letters, vol. 18, No. 17, Sep. 1, 1993.
Silva et al: "Extended Range, Rapid Scanning Optical Delay Line for Biomedical Interferometric Imaging", Electronics Letters, IEE Stevenage, GB vol. 35, No. 17, Aug. 19, 1999.
Zhang and Chen, "Fourier Domain Functional Optical Coherence Tomography," 2005, Proc. of SPIE vol. 5771.*
Liptak David C. et al., (2007) "On the Development of a Confocal Rayleigh-Brillouin Microscope" *American Institute of Physics* vol. 78, 016106.
Invitation of Pay Additional Fees mailed Jul. 20, 2008 for International Application No. PCT/US2007/081982.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "Increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Notice of Allowance mailed Jun. 4, 2008 for U.S. Appl. No. 11/174,425.
European communication dated May 15, 2008 for European patent application No. 05819917.5.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", Optics *IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
Fujimoto et al., "High Resolution in Vivo Intra-Arterial Imaging with Optical Coherence Tomography," *Official Journal of the British Cardiac Society*, vol. 82, pp. 128-133 Heart, 1999.
D. Huang et al., "Optical Coherence Tomography," *Science*, vol. 254, pp. 1178-1181, Nov. 1991.
Rollins, et al., "In Vivo Video Rate Optical Coherence Tomography," *Optics Express*, vol. 3, pp. 219-229, Sep. 1998.
Saxer, et al., High Speed Fiber-Based Polarization-Sensitive Optical Coherence Tomography of in Vivo Human Skin, *Optical Society of America*, vol. 25, pp. 1355-1357, Sep. 2000.
Oscar Eduardo Martinez, "3000 Times Grating Compress or with Positive Group Velocity Dispersion," *IEEE*, vol. QE-23, pp. 59-64, Jan. 1987.
Kulkarni, et al., "Image Enhancement in Optical Coherence Tomography Using Deconvolution," *Electronics Letters*, vol. 33, pp. 1365-1367, Jul. 1997.

(56) References Cited

OTHER PUBLICATIONS

Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Images," *Journal of Biomedical Optics*, vol. 4, pp. 125-136, Jan. 1999.
W. Drexler et al., "In Vivo Ultrahigh-Resolution Optical Coherence Tomography," *Optics Letters* vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.
Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.
Andretzky, P. et al., "Optical Coherence Tomography by Spectral Radar: Improvement of Signal-to-Noise Ratio," *The International Society for Optical Engineering*, USA, vol. 3915, 2000.
Ballif, J. et al., "Rapid and Scalable Scans at 21 m/s in optical Low-Coherence Reflectometry," *Optics Letters*, vol. 22, pp. 757-759, Jun. 1997.
Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.
Beaud, P. et al., "Optical Reflectometry with Micrometer Resolution for the Investigation of Integrated Optical-Devices," *Leee Journal of Quantum Electronics*, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.
Brinkmeyer, E. et al., "Efficient Algorithm for Non-Equidistant Interpolation of Sampled Data," *Electronics Letters*, vol. 28, p. 693, Mar. 1992.
Brinkmeyer, E. et al., "High-Resolution OCDR in Dispersive Wave-Guides," *Electonics Letters*, vol. 26, pp. 413-414, Mar. 1990.
Chinn, S.R. et al., "Optical Coherence Tomography Using a Frequency-Tunable Optical Source," *Optics Letters*, vol. 22, pp. 340-342, Mar. 1997.
Danielson, B.L. et al., "Absolute Optical Ranging Using Low Coherence Interferometry," *Applied Optics*, vol. 30, p. 2975, Jul. 1991.
Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.
Eickhoff, W. et al., "Optical Frequency-Domain Reflectometry in Single-Mode Fiber," *Applied Physics Letters*, vol. 39, pp. 693-695, 1981.
Fercher, Adolf "Optical Coherence Tomography," *Journal of Biomedical Optics*, vol. 1, pp. 157-173, Apr. 1996.
Ferreira, L.A. et al., "Polarization-Insensitive Fiberoptic White-Light Interferometry," *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.
Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B* (*Optical Physics*), vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.
Ivanov, A. P. et al., "New Method for High-Range Resolution Measurements of Light Scattering in Optically Dense Inhomogeneous Media," *Optics Letters*, vol. 1, pp. 226-228, Dec. 1977.
Ivanov, A. P. et al., "Interferometric Study of the Spatial Structure of a Light-Scattering Medium," *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.
Kersey, A. D. et al., "Adaptive Polarization Diversity Receiver Configuration for Coherent Optical Fiber Communications," *Electronics Letters*, vol. 25, pp. 275-277, Feb. 1989.
Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.
Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.
Leitgeb, R. et al., "Spectral measurement of Absorption by Spectroscopic Frequency-Domain Optical Coherence Tomography," *Optics Letters*, vol. 25, pp. 820-822, Jun. 2000.
Lexer, F. et al., "Wavelength-Tuning Interferometry of Intraocular Distances," *Applied Optics*, vol. 36, pp. 6548-6553, Sep. 1997.
Mitsui, Takahisa, "Dynamic Range of Optical Reflectometry with Spectral Interferometry," *Japanese Journal of Applied Physics Part 1—Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.
Okoshi,Takanori, "Polarization-State Control Schemes for Heterodyne or Homodyne Optical Fiber Communications," *Journal of Lightwave Technology*, vol. LT-3, pp. 1232-1237, Dec. 1995.
Passy, R. et al., "Experimental and Theoretical Investigations of Coherent OFDR with Semiconductor-Laser Sources," *Journal of Lightwave Technology*, vol. 12, pp. 1622-1630, Sep. 1994.

(56) References Cited

OTHER PUBLICATIONS

Podoleanu, Adrian G., "Unbalanced Versus Balanced Operation in an Optical Coherence Tomography System," *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.
Schmitt, J. M. et al, "Measurement of Optical-Properties of Biological Tissues by Low-Coherence Reflectometry," *Applied Optics*, vol. 32, pp. 6032-6042, Oct. 1993.
Silberberg, Y. et al., "Passive-Mode Locking of a Semiconductor Diode-Laser," *Optics Letters*, vol. 9, pp. 507-509, Nov. 1984.
Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.
Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.
Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.
Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.
Swanson, E. A. et al., "High-Speed Optical Coherence Domain Reflectometry," *Optics Letters*, vol. 17, pp. 151-153, Jan. 1992.
Takada, K. et al., "High-Resolution OFDR with Incorporated Fiberoptic Frequency Encoder," *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.
Takada, Kazumasa et al., "New Measurement System for Fault Location in Optical Wave-Guide Devices Based on an Interometric-Technique," *Applied Optics*, vol. 26, pp. 1603-1606, May 1987.
Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.
Trutna, W. R. et al., "Continuously Tuned External-Cavity Semiconductor-Laser," *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.
Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.
Youngquist, Robert C. et al., "Optical Coherence-Domain Reflectometry—A New Optical Evaluation Technique," *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic Tunable Filter," *IEEE Journal of Selected Topicsin Quantum Electronics*, vol. 3, pp. 1087-1096, Aug. 1997.
Yun, S. H. et al., "Interrogation of Fiber Grating Sensor Arrays with a Wavelength-Swept Fiber Laser," *Optics Letters*, vol. 23, pp. 843-845, Jun. 1998.
Yung, K. M., "Phase-Domain Processing of Optical Coherence Tomography Images," *Journal of Biomedical Optics*, vol. 4, pp. 125-136, Jan. 1999.
Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers," *Journal of Lightwave Technology*, vol. 13, pp. 62-66, Jan. 1995.
Victor S. Y. Lin et al., "A Porous Silicon-Based Optical Interferometric Biosensor," *Science Magazine*, vol. 278, pp. 840-843, Oct. 31, 1997.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6, No. 4, Oct. 2001, pp. 474-479.
Roth, Jonathan E. et al., "Simplified Method for Polarization-Sensitive Optical Coherence Tomography," *Optics Letters*, vol. 26, No. 14, Jul. 15, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wong, Brian J.F. et al., "Optical Coherence Tomography of the Rat Cochlea," *Journal of Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Bréhonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

(56) References Cited

OTHER PUBLICATIONS

De Boer, Johannes F. et al., "Two-Dimensional Birefringence Imaging in Biological Tissue by Polarization-Sensitive Optical Coherence Tomography," Optics Letters, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.
Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.
Schmitt, J.M. et al., "Cross-Polarized Backscatter in Optical Coherence Tomography of Biological Tissue," *Optics Letters*, vol. 23, No. 13, Jul. 1, 1998, pp. 1060-1062.
Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.
Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of in Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved with Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Material Characterisation and Strain-Field Mapping," Applied Physics A 76, Materials Science & Processing, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.
Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin in Vivo," 2004, *Optical Society of America.*
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al., "Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," Physics in Medicine and Biology, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N. A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

(56) References Cited

OTHER PUBLICATIONS

Park, B. Hyle et al., Comment on "Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc*. 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Journal of Tomography," *Biomedical Optics*, vol. 9, No. 1, Jan./Feb. 2004, pp. 121-125.
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.
Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Acioli, L. H., M. Ulman, et al. (1991). "Femtosecond Temporal Encoding in Barium-Titanate." *Optics Letters* 16(24): 1984-1986.
Aigouy, L., A. Lahrech, et al. (1999). "Polarization effects in apertureless scanning near-field optical microscopy: an experimental study." Optics Letters 24(4): 187-189.
Akiba, M., K. P. Chan, et al. (2003). "Full-field optical coherence tomography by two-dimensional heterodyne detection with a pair of CCD cameras." *Optics Letters* 28(10): 816-818.
Akkin, T., D. P. Dave, et al. (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensitivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.
Antcliff, R. J., T. J. ffytche, et al. (2000). "Optical coherence tomography of melanocytoma." *American Journal of Ophthalmology* 130(6): 845-7.
Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.
Anvari, B., T. E. Milner, et al. (1995). "Selective Cooling of Biological Tissues—Application for Thermally Mediated Therapeutic Procedures." *Physics in Medicine and Biology* 40(2):241-252.
Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.
Arend, O., M. Ruffer, et al. (2000). "Macular circulation in patients with diabetes mellitus with and without arterial hypertension." *British Journal of Ophthalmology* 84(12): 1392-1396.
Arimoto, H. and Y. Ohtsuka (1997). "Measurements of the complex degree of spectral coherence by use of a wave-front-folded interferometer." *Optics Letters* 22(13): 958-960.
Azzolini, C., F. Patelli, et al. (2001). "Correlation between optical coherence tomography data and biomicroscopic interpretation of idiopathic macular hole." *American Journal of Ophthalmology* 132(3): 348-55.
Baba, T., K. Ohno-Matsui, et al. (2002). "Optical coherence tomography of choroidal neovascularization in high myopia." *Acta Ophthalmoloqica Scandinavica* 80(1): 82-7.
Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE* , 2925: p. 298-303.
Baney, D. M. And W. V. Sorin (1993). "Extended-Range Optical Low-Coherence Reflectometry Using a Recirculating Delay Technique." *Ieee Photonics Technology Letters* 5(9): 1109-1112.
Baney, D. M., B. Szafraniec, et al. (2002). "Coherent optical spectrum analyzer." *Ieee Photonics Technology Letters* 14(3): 355-357.
Barakat, R. (1981). "Bilinear Constraints between Elements of the 4by4 Mueller-Jones Transfer-Matrix of Polarization Theory." *Optics Communications* 38(3): 159-161.
Barakat, R. (1993). "Analytic Proofs of the Arago-Fresnel Laws for the Interference of Polarized-Light." *Journal of the Optical Society of America a-Optics Image Science and Vision* 10(1): 180-185.
Barbastathis, G. and D. J. Brady (1999). "Multidimensional tomographic imaging using volume holography." *Proceedings of the Ieee* 87(12): 2098-2120.
Bardal, S., A. Kamal, et al. (1992). "Photoinduced Birefringence in Optical Fibers—a Comparative-Fibers Study of Low-Birefringence and High-Birefringence Fibers." *Optics Letters* 17(6): 411-413.
Barsky, S. H., S. Rosen, et al. (1980). "Nature and Evolution of Port Wine Stains—Computer-Assisted Study." *Journal of Investigative Dermatology* 74(3): 154-157.
Barton, J. K., J. A. Izatt, et al. (1999). "Three-dimensional reconstruction of blood vessels from in vivo color Doppler optical coherence tomography images." Dermatology 198(4):355-361.
Barton, J. K., A. Rollins, et al. (2001). "Photothermal coagulation of blood vessels: a comparison of high-speed optical coherence tomography and numerical modelling." *Physics in Medicine and Biology* 46.
Barton, J. K., A. J. Welch, et al. (1998). "Investigating pulsed dye laser-blood vessel interaction with color Doppler optical coherence tomography." *Optics Express* 3.
Bashkansky, M., M. D. Duncan, et al. (1997). "Subsurface defect detection in ceramics by high-speed high-resolution optical coherent tomography." *Optics Letters* 22 (1): 61-63.
Bashkansky, M. and J. Reintjes (2000). "Statistics and reduction of speckle in optical coherence tomography." *Optics Letters* 25(8): 545-547.
Baumgartner, A., S. Dichtl, et al. (2000). "Polarization-sensitive optical coherence tomography of dental structures." *Caries Research* 34(1): 59-69.

(56) References Cited

OTHER PUBLICATIONS

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.
Baumgartner, A., C. K. Hitzenberger, et al. (1998). "Signal and resolution enhancements in dual beam optical coherence tomography of the human eye." *Journal of Biomedical Optics* 3(1): 45-54.
Beaurepaire, E., P. Gleyzes, et at. (1998). *Optical coherence microscopy for the in-depth study of biological structures: System based on a parallel detection scheme*, Proceedings of SPIE—The International Society for Optical Engineering.
Beaurepaire, E., L. Moreaux, et al. (1999). "Combined scanning optical coherence and two-photon-excited fluorescence microscopy." *Optics Letters* 24(14): 969-971.
Bechara, F. G., T. Gambichler, et al. (2004). "Histomorphologic correlation with routine histology and optical coherence tomography." *Skin Research and Technology* 10 (3): 169-173.
Bechmann, M., M. J. Thiel, et al. (2000). "Central corneal thickness determined with optical coherence tomography in various types of glaucoma. [see comments]." *British Journal of Ophthalmology* 84(11): 1233-7.
Bek, T. and M. Kandi (2000). "Quantitative anomaloscopy and optical coherence tomography scanning in central serous chorioretinopathy." *Acta Ophthalmologica Scandinavica* 78(6): 632-7.
Benoit, A. M., K. Naoun, et al. (2001). "Linear dichroism of the retinal nerve fiber layer expressed with Mueller matrices." *Applied Optics* 40(4): 565-569.
Bicout, D., C. Brosseau, et al. (1994). "Depolarization of Multiply Scattered Waves by Spherical Diffusers—Influence of the Size Parameter." *Physical Review* E 49(2): 1767-1770.
Blanchot, L., M. Lebec, et al. (1997). *Low-coherence in depth microscopy for biological tissues imaging: Design of a real time control system*. Proceedings of SPIE—The International Society for Optical Engineering.
Blumenthal, E. Z. and R. N. Weinreb (2001). "Assessment of the retinal nerve fiber layer in clinical trials of glaucoma neuroprotection. [Review][36 refs]." *Survey of Ophthalmology* 45(Suppl 3):S305-12; discussion S332-4.
Blumenthal, E. Z., J. M. Williams, et al. (2000). "Reproducibility of nerve fiber layer thickness measurements by use of optical coherence tomography." *Ophthalmology* 107(12): 2278-82.
Boppart, S. A., B. E. Bouma, et al. (1996). "Imaging developing neural morphology using optical coherence tomography." *Journal of Neuroscience Methods* 70.
Boppart, S. A., B. E. Bouma, et al. (1997). "Forward-imaging instruments for optical coherence tomography." *Optics Letters* 22.
Boppart, S. A., B. E. Bouma, et al. (1998). "Intraoperative assessment of microsurgery with three-dimensional optical coherence tomography." *Radiology* 208: 81-86.
Boppart, S. A., J. Herrmann, et al. (1999). "High-resolution optical coherence tomography-guided laser ablation of surgical tissue." *Journal of Surgical Research* 82(2): 275-84.
Bouma, B. E. and J. G. Fujimoto (1996). "Compact Kerr-lens mode-locked resonators." *Optics Letters* 21. 134-136.
Bouma, B. E., L. E. Nelson, et al. (1998). "Optical coherence tomographic imaging of human tissue at 1.55 82 m and 1.81 μm using Er and Tm-doped fiber sources." *Journal of Biomedical Optics*3. 76-79.
Bouma, B. E., M. Ramaswamy-Paye, et al. (1997). "Compact resonator designs for mode-locked solid-state lasers." *Applied Physics B* (*Lasers and Optics*) B65. 213-220.
Bouma, B. E. and G. J. Teamey (2002). "Clinical imaging with optical coherence tomography." *Academic Radiology* 9(8): 942-953.
Bouma, B. E., G. J. Tearney, et al. (1996). "Self-phase-modulated Kerr-lens mode-locked Cr:forsterite laser source for optical coherence tomography." *Optics Letters* 21(22): 1839.
Bouma, B. E., G. J. Tearney, et al. (2000). "High-resolution imaging of the human esophagus and stomach in vivo using optical coherence tomography." *Gastrointestinal Endoscopy* 51(4): 467-474.
Bouma, B. E., G. J. Tearney, et al. (2003). "Evaluation of intracoronary stenting by intravascular optical coherence tomography." *Heart* 89(3): 317-320.
Bourquin, S., V. Monterosso, et al. (2000). "Video-rate optical low-coherence reflectometry based on a linear smart detector array." *Optics Letters* 25(2): 102-104.
Bourquin, S., P. Seitz, et al. (2001). "Optical coherence topography based on a two-dimensional smart detector array." *Optics Letters* 26(8): 512-514.
Bouzid, A., M. A. G. Abushagur, et al. (1995). "Fiber-optic four-detector polarimeter." *Optics Communications* 118(3-4): 329-334.
Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.
Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.
Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.
Brand, S., J. M. Poneros, et al. (2000). "Optical coherence tomography in the gastrointestinal tract." *Endoscopy* 32(10): 796-803.
Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.
Brezinski, M. E., G. J. Tearney, et al. (1996). "Imaging of coronary artery microstructure (in vitro) with optical coherence tomography." *American Journal of Cardiology* 77 (1): 92-93.
Brezinski, M. E., G. J. Teamey, et al. (1996). "Optical coherence tomography for optical biopsy—Properties and demonstration of vascular pathology." *Circulation* 93(6): 1206-1213.
Brezinski, M. E., G. J. Teamey, et al. (1997). "Assessing atherosclerotic plaque morphology: Comparison of optical coherence tomography and high frequency intravascular ultrasound." *Heart* 77(5): 397-403.
Brink, H. B. K. and G. J. Vanblokland (1998). "Birefringence of the Human Foveal Area Assessed Invivo with Mueller-Matrix Ellipsometry." *Journal of the Optical Society of America a-Optics Image Science and Vision* 5(1): 49-57.
Brosseau, C. and D. Bicout (1994). "Entropy Production in Multiple-Scattering of Light by a Spatially Random Medium." *Physical Review E* 50(6): 4997-5005.
Burgoyne, C. F., D. E. Mercante, et al. (2002). "Change detection in regional and volumetric disc parameters using longitudinal confocal scanning laser tomography." *Ophthalmology* 109(3): 455-66.
Candido, R. and T. J. Allen (2002). "Haemodynamics in microvascular complications in type 1 diabetes." *Diabetes-Metabolism Research and Reviews* 18(4): 286-304.
Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.
Cense, B., N. Nassif, et al. (2004). "Ultrahigh-Resolution High-Speed Retinal Imaging Using Spectral-Domain Optical Coherence Tomography." *Optics Express* 12(11): 2435-2447.
Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.
Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.
Chartier, T., A. Hideur, et al. (2001). "Measurement of the elliptical birefringence of single-mode optical fibers." *Applied Optics* 40(30): 5343-5353.

(56) References Cited

OTHER PUBLICATIONS

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al. (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of SelectedTopics in Quantum Electronics* 5(4): 1134-1142.
Cheong, W. F., S. A. Prahl, et al. (1990). "A Review of the Optical-Properties of Biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho, S. H., B. E. Bouma, et al. (1999). "Low-repetition-rate high-peak-power Kerr-lens mode-locked Ti:AI/sub 2/0/sub 3/ laser with a multiple-pass cavity." *Optics Letters* 24(6): 417-419.
Choma, M. A., M. V. Sarunic, et al. (2003). "Sensitivity advantage of swept source and Fourier domain optical coherence tomography." *Optics Express* 11(18): 2183-2189.
Choma, M. A., C. H. Yang, et al. (2003). "Instantaneous quadrature low-coherence interferometry with 3×3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 108 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama-Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.
Dave, D. P. and T. E. Milner (2000), "Doppler-angle measurement in highly scattering media." *Optics Letters* 25(20): 1523-1525.
de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.
de Boer, J. F., C. E. Saxer, et al. (2001). "Stable carrier generation and phase-resolved digital data processing in optical coherence tomography." *Applied Optics* 40(31): 5787-5790.
Degroot, P. and L. Deck (1993). "3-Dimensional Imaging by Sub-Nyquist Sampling of White-Light Interferograms." *Optics Letters* 18(17): 1462-1464.
Denk, W., J. H. Strickler, et al. (1990). "2-Photon Laser Scanning Fluorescence Microscopy." *Science* 248(4951): 73-76.
Descour, M. R., A. H. O. Karkkainen, et al. (2002). "Toward the development of miniaturized Imaging systems for detection of pre-cancer." *Ieee Journal of Quantum Electronics* 38(2): 122-130.
Dettwiller, L. (1997). "Polarization state interference: A general investigation." *Pure and Applied Optics* 6(1): 41-53.
DiCarlo, C. D., W. P. Roach, et al. (1999). "Comparison of optical coherence tomography imaging of cataracts with histopathology." *Journal of Biomedical Optics* 4.
Ding, Z., Y. Zhao, et al. (2002). "Real-time phase-resolved optical coherence tomography and optical Doppler tomography." *Optics Express* 10(5): 236-245.
Dobrin, P. B. (1996). "Effect of histologic preparation on the cross-sectional area of arterial rings." *Journal of Surgical Research* 61(2): 413-5.
Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.
Drexler, W., A. Baumgartner, et al. (1997). "Biometric investigation of changes in the anterior eye segment during accommodation." *Vision Research* 37(19): 2789-2800.
Drexler, W., A. Baumgartner, et al. (1997). "Submicrometer precision biometry of the anterior segment of the human eye." *Investigative Opthalmology & Visual Science* 38(7): 1304-1313.
Drexler, W., A. Baumgartner, et al. (1998). "Dual beam optical coherence tomography: signal identification for ophthalmologic diagnosis." *Journal of Biomedical Optics* 3 (1): 55-65.
Drexler, W., O. Findl, et al. (1998). "Partial coherence interferometry: A novel approach to biometry in cataract surgery." *American Journal of Ophthalmology* 126(4): 524-534.
Drexler, W., O. Findl, et al. (1997). "Clinical feasibility of dual beam optical coherence topography and tomography for ophthalmologic diagnosis." *Investigative Ophthalmology& Visual Science* 38(4): 1038-1038.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.
Drexler, W., C. K. Hitzenberger, et al. (1995). "Measurement of the Thickness of Fundus Layers by Partial Coherence Tomography." *Optical Engineering* 34(3): 701-710.
Drexler, W., U. Morgner, et al. (2001). "Ultrahigh-resolution ophthalmic optical coherence tomography." *Nature Medicine* 7(4): 502-507.
Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

(56) References Cited

OTHER PUBLICATIONS

Drexler, W., H. Sattmann, et al. (2003). "Enhanced visualization of macular pathology with the use of ultrahigh-resolution optical coherence tomography." *Archives of Ophthalmology* 121(5): 695-706.
Drexler, W., D. Stamper, et al. (2001). "Correlation of collagen organization with polarization sensitive imaging of in vitro cartilage: implications for osteoarthritis." *Journal of Rheumatology* 28(6): 1311-8.
Droog, E. J., W. Steenbergen, et al. (2001). "Measurement of depth of burns by laser Doppler perfusion imaging." *Burns* 27(6): 561-8.
Dubois, A., K. Grieve, et al. (2004). "Ultrahigh-resolution full-field optical coherence tomography." *Applied Optics* 43(14): 2874-2883.
Dubois, A., L. Vabre, et al. (2002). "High-resolution full-field optical coherence tomography with a Linnik microscope." *Applied Optics* 41(4):805-812.
Ducros, M., M. Laubscher, et al. (2002). "Parallel optical coherence tomography in scattering samples using a two-dimensional smart-pixel detector array." *Optics Communications* 202(1-3): 29-35.
Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.
Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.
Eigensee, A., G. Haeusler, et al. (1996). "New method of short-coherence interferometry in human skin (in vivo) and in solid vol. scatterers." *Proceedings of SPIE—The International Society for Optical Engineering* 2925: 169-178.
Eisenbeiss, W., J. Marotz, et al. (1999). "Reflection-optical multispectral imaging method for objective determination of burn depth." *Burns* 25(8): 697-704.
Elbaum, M., M. King, et al. (1972). "Wavelength-Diversity Technique for Reduction of Speckle Size." *Journal of the Optical Society of America* 62(5): 732-&.
Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.
Essenpreis, M., C. E. Elwell, et al. (1993). "Spectral Dependence of Temporal Point Spread Functions in Human Tissues." *Applied Optics* 32(4): 418-425.
Eun, H. C. (1995). "Evaluation of skin blood flow by laser Doppler flowmetry. [Review][151 refs]." *Clinics in Dermatology* 13(4): 337-47.
Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.
Feldchtein, F. I., G. V. Gelikonov, et al. "In vivo OCT imaging of hard and soft tissue of the oral cavity." *Optics Express* 3(6): 239-250. (1998).
Feldchtein, F. I., G. V. Gelikonov, et al. "Endoscopic applications of optical coherence tomography." *Optics Express* 3(6): 257-270. (1998).
Fercher, A. F., W. Drexler, et al. (1997). "Optical ocular tomography." *Neuro-Ophthalmology* 18(2): 39-49.
Fercher, A. F., W. Drexler, et al. (1994). *Measurement of optical distances by optical spectrum modulation*. Proceedings of SPIE—The International Society for Optical Engineering.
Fercher, A. F., W. Drexler, et al. (2003). "Optical coherence tomography—principles and applications." *Reports on Progress in Physics* 66(2): 239-303.
Fercher, A. F., C. Hitzenberger, et al. (1991). "Measurement of Intraocular Optical Distances Using Partially Coherent Laser-Light." *Journal of Modern Optics* 38(7): 1327-1333.
Fercher, A. F., C. K. Hitzenberger, et al. (1996). *Ocular partial coherence interferometry*. Proceedings of SPIE—The International Society for Optical Engineering.
Fercher, A. F., C. K. Hitzenberger, et al. (1993). "In-Vivo Optical Coherence Tomography." *American Journal of Ophthalmology* 116(1): 113-115.
Fercher, A. F., C. K. Hitzenberger, et al. (1994). *In-vivo dual-beam optical coherence tomography*. Proceedings of SPIE—The International Society for Optical Engineering.
Fercher, A. F., C. K. Hitzenberger, et al. (1995). "Measurement of Intraocular Distances by Backscattering Spectral Interferometry." *Optics Communications* 117(1-2): 43-48.
Fercher, A. F., C. K. Hitzenberger, et al. (2000). "A thermal light source technique for optical coherence tomography." *Optics Communications* 185(1-3): 57-64.
Fercher, A. F., C. K. Hitzenberger, et al. (2001). "Numerical dispersion compensation for Partial Coherence Interferometry and Optical Coherence Tomography." *Optics Express* 9(12): 610-615.
Fercher, A. F., C. K. Hitzenberger, et al. (2002) "Dispersion compensation for optical coherence tomography depth-scan signals by a numerical technique." *Optics Communications* 204(1-6): 67-74.
Fercher, A. F., H. C. Li, et al. (1993). "Slit Lamp Laser-Doppler Interferometer." *Lasers in Surgery and Medicine* 13(4): 447-452.
Fercher, A. F., K. Mengedoht, et at. (1988). "Eye-Length Measurement by Interferometry with Partially Coherent-Light." *Optics Letters* 13(3): 186-188.
Ferro, P., M. Haelterman, et al. (1991). "All-Optical Polarization Switch with Long Low-Birefringence Fiber." *Electronics Letters* 27(16): 1407-1408.
Fetterman, M. R., D. Goswami, et al. (1998). "Ultrafast pulse shaping: amplification and characterization." *Optics Express* 3(10): 366-375.
Findl, O., W. Drexler, et al. (2001). "Improved prediction of intraocular lens power using partial coherence interferometry." *Journal of Cataract and Refractive Surgery* 27 (6): 861-867.
Fork, R. L., C. H. B. Cruz, et al. (1987). "Compression of Optical Pulses to 6 Femtoseconds by Using Cubic Phase Compensation." *Optics Letters* 12(7): 483-485.
Foschini, G. J. and C. D. Poole (1991). "Statistical-Theory of Polarization Dispersion in Single-Mode Fibers." *Journal of Lightwave Technology* 9(11): 1439-1456.
Francia, C., F. Bruyere, et al. (1998). "PMD second-order effects on pulse propagation in single-mode optical fibers." *Ieee Photonics Technology Letters* 10(12): 1739-1741.
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto, J. G., M. E. Brezinski, et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Optical Engineering* 20(1): 25-30.
Galtarossa, A., L. Palmieri, et al. (2000). "Statistical characterization of fiber random birefringence." *Optics Letters* 25(18):1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikonov, V. M., G. V. Gelikonov, et al. (1995). "Coherent Optical Tomography of Microscopic Inhomogeneities in Biological Tissues." *Jetp Letters* 61(2): 158-162.
George, N. and A. Jain (1973). "Speckle Reduction Using Multiple Tones of Illumination." *Applied Optics* 12(6): 1202-1212.

(56) References Cited

OTHER PUBLICATIONS

Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a-Optics Image Science and Vision* 17(2): 328-334.
Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.
Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.
Greaney, M. J., D. C. Hoffman, et al. (2002). "Comparison of optic nerve imaging methods to distinguish normal eyes from those with glaucoma." *Investigative Opthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-μm Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmology* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in volume scatterers with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interferometric Ellipsometry and Precision Reflectometry." *Journal of Physics E-Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Topography of diabetic macular edema with optical coherence tomography." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Welle (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vivo, ultrahigh-resolution optical coherence tomography." *Optics Letters* 29(19): 2261-2263.
Hirakawa, H., H. Iijima, et al. (1999). "Optical coherence tomography of cystoid macular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.

(56) References Cited

OTHER PUBLICATIONS

Hitzenberger, C. K., A. Baumgartner, et al. (1999). "Dispersion effects in partial coherence interferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154 (4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., A. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Hotate, K. and T. Okugawa (1994). "Optical Information-Processing by Synthesis of the Coherence Function." *Journal of Lightwave Technology* 12(7): 1247-1255.
Hourdakis, C. J. and A. Perris (1995). "A Monte-Carlo Estimation of Tissue Optical-Properties for Use in Laser Dosimetry." *Physics in Medicine and Biology* 40(3): 351-364.
Hu, Z., F. Li, et al. (2000). "Wavelength-tunable narrow-linewidth semiconductor fiber-ring laser." *IEEE Photonics Technology Letters* 12(8): 977-979.
Huang, F., W. Yang, et al. (2001). "Quadrature spectral interferometric detection and pulse shaping." *Optics Letters* 26(6): 382-384.
Huang, X. R. and R. W. Knighton (2002). "Linear birefringence of the retinal nerve fiber layer measured in vitro with a multispectral imaging micropolarimeter." *Journal of Biomedical Optics* 7(2): 199-204.
Huber, R., M. Wojtkowski, et al. (2005). "Amplified, frequency swept lasers for frequency domain reflectometry and OCT imaging: design and scaling principles." *Optics Express* 13(9): 3513-3528.
Hunter, D. G., J. C. Sandruck, et al. (1999). "Mathematical modeling of retinal birefringence scanning." *Journal of the Optical Society of America a-Optics Image Science and Vision* 16(9): 2103-2111.
Hurwitz, H. H. and R. C. Jones (1941). "A new calculus for the treatment of optical systems II. Proof of three general equivalence theorems." *Journal of the Optical Society of America* 31(7): 493-499.
Huttner, B., C. De Barros, et al. (1999). "Polarization-induced pulse spreading in birefringent optical fibers with zero differential group delay." *Optics Letters* 24(6): 370-372.
Huttner, B., B. Gisin, et al. (1999). "Distributed PMD measurement with a polarization-OTDR in optical fibers." *Journal of Lightwave Technology* 17(10): 1843-1848.
Huttner, B., J. Reecht, et al. (1998). "Local birefringence measurements in single-mode fibers with coherent optical frequency-domain reflectometry." *Ieee Photonics Technology Letters* 10(10): 1458-1460.
Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.
Hyde, S. C. W., N. P. Barry, et al. (1995). "Depth-Resolved Holographic Imaging through Scattering Media by Photorefraction." *Optics Letters* 20(11): 1331-1333.
Iftimia, N. V., B. E. Bouma, et al. (2004). "Adaptive ranging for optical coherence tomography." *Optics Express* 12(17): 4025-4034.
Iida, T., N. Hagimura, et al. (2000). "Evaluation of central serous chorioretinopathy with optical coherence tomography." *American Journal of Ophthalmology* 129(1): 16-20.
Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.
Indebetouw, G. and P. Klysubun (2000). "Imaging through scattering media with depth resolution by use of low-coherence gating in spatiotemporal digital holography." *Optics Letters* 25(4): 212-214.
Ip, M. S., B. J. Baker, et al. (2002). "Anatomical outcomes of surgery for idiopathic macular hole as determined by optical coherence tomography." *Archives of Ophthalmology* 120(1): 29-35.
Ismail, R., V. Tanner, et al. (2002). "Optical coherence tomography imaging of severe commotio retinae and associated macular hole." *British Journal of Ophthalmology* 86(4): 473-4.
Izatt, J. A., M. R. Hee, et al. (1994). "Optical Coherence Microscopy in Scattering Media." *Optics Letters* 19(8): 590-592.
Izatt, J. A., M. R. Hee, et al. (1994). "Micrometer-scale resolution imaging of the anterior eye in vivo with optical coherence tomography." *Archives of Ophthalmology* 112 (12): 1584-9.
Izatt, J. A., M. D. Kulkami, et al. (1997). "In vivo bidirectional color Doppler flow imaging of picoliter blood volumes using optical coherence tomography." *Optics Letters* 22(18): 1439-1441.
Izatt, J. A., M. D. Kulkarni, et al. (1996). "Optical coherence tomography and microscopy in gastrointestinal tissues." *IEEE Journal of Selected Topics in Quantum Electronics* 2(4): 1017.
Jacques, S. L., J. S. Nelson, et al. (1993). "Pulsed Photothermal Radiometry of Port-Wine-Stain Lesions." *Applied Optics* 32(13): 2439-2446.
Jacques, S. L., J. R. Roman, et al. (2000). "Imaging superficial tissues with polarized light." *Lasers in Surgery and Medicine* 26(2): 119-129.
Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.
Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S.
Jang, I. K., G. J. Tearney, et al. (2000). "Comparison of optical coherence tomography and intravascular ultrasound for detection of coronary plaques with large lipid-core in living patients." *Circulation* 102(18): 509-509.
Jeng, J. C., A. Bridgeman, et al. (2003). "Laser Doppler imaging determines need for excision and grafting in advance of clinical judgment: a prospective blinded trial." *Burns* 29(7): 665-670.
Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.
Johnson, C. A., J. L. Kellner, et al. (2002). "Baseline visual field characteristics in the ocular hypertension treatment study." *Ophthalmology* 109(3): 432-7.
Jones, R. C. (1941). "A new calculus for the treatment of optical systems III. The Sohncke theory of optical activity." *Journal of the Optical Society of America* 31 (7): 500-503.

(56) References Cited

OTHER PUBLICATIONS

Jones, R. C. (1941). "A new calculus for the treatment of optical systems I. Description and discussion of the calculus." *Journal of the Optical Society of America* 31(7): 488-493.
Jones, R. C. (1942). "A new calculus for the treatment of optical systems. IV." *Journal of the Optical Society of America* 32(8): 486-493.
Jones, R. C. (1947). "A New Calculus for the Treatment of Optical Systems .6. Experimental Determination of the Matrix." *Journal of the Optical Society of America* 37(2): 110-112.
Jones, R. C. (1947). "A New Calculus for the Treatment of Optical Systems .5. A More General Formulation, and Description of Another Calculus." *Journal of the Optical Society of America* 37(2): 107-110.
Jones, R. C. (1948). "A New Calculus for the Treatment of Optical Systems .7. Properties of the N-Matrices." *Journal of the Optical Society of America* 38(8): 671-685.
Jones, R. C. (1956). "New Calculus for the Treatment of Optical Systems .8. Electromagnetic Theory." *Journal of the Optical Society of America* 46(2): 126-131.
Jopson, R. M., L. E. Nelson, et al. (1999). "Measurement of second-order polarization-mode dispersion vectors in optical fibers." *Ieee Photonics Technology Letters* 11 (9): 1153-1155.
Jost, B. M., A. V. Sergienko, et al. (1998). "Spatial correlations of spontaneously down-converted photon pairs detected with a single-photon-sensitive CCD camera." *Optics Express* 3(2): 81-88.
Kaplan, B., E. Compain, et al. (2000). "Phase-modulated Mueller ellipsometry characterization of scattering by latex sphere suspensions." *Applied Optics* 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.
Kasuga, Y., J. Arai, et al. (2000). "Optical coherence tomograghy to confirm early closure of macular holes." *American Journal of Ophthalmology* 130(5): 675-6.
Kaufman, T., S. N. Lusthaus, et al. (1990). "Deep Partial Skin Thickness Burns—a Reproducible Animal-Model to Study Burn Wound-Healing." *Burns* 16(1): 13-16.
Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.
Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.
Kesen, M. R., G. L. Spaeth, et al. (2002). "The Heidelberg Retina Tomograph vs clinical impression in the diagnosis of glaucoma." *American Journal of Ophthalmology* 133(5): 613-6.
Kienle, A. and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand, et al. (1994). "Differential Vascular-Response to Laser Photothermolysis." *Journal of Investigative Dermatology* 103(5): 693-700.
Kloppenberg, F. W. H., G. Beerthuizen, et al. (2001). "Perfusion of burn wounds assessed by Laser Doppler Imaging is related to burn depth and healing time." *Burns* 27(4): 359-363.
Knighton, R. W. and X. R. Huang (2002). "Analytical methods for scanning laser polarimetry." *Optics Express* 10(21): 1179-1189.
Knighton, R. W., X. R. Huang, et al. (2002). "Analytical model of scanning laser polarimetry for retinal nerve fiber layer assessment." *Investigative Opthalmology & Visual Science* 43(2): 383-392.
Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.
Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.
Knuttel, A. and J. M. Schmitt (1993). "Stationary Depth-Profiling Reflectometer Based on Low-Coherence Interferometry." *Optics Communications* 102(3-4): 193-198.
Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.
Kobayashi, M., H. Hanafusa, et al. (1991). "Polarization-Independent Interferometric Optical-Time-Domain Reflectometer." *Journal of Lightwave Technology* 9(5): 623-628.
Kolios, M. C., M. D. Sherar, et al. (1995). "Large Blood-Vessel Cooling in Heated Tissues—a Numerical Study." *Physics in Medicine and Biology* 40(4): 477-494.
Koozekanani, D., K. Boyer, et al. (2001). "Retinal thickness measurements from optical coherence tomography using a Markov boundary model." *Ieee Transactions on Medical Imaging* 20(9): 900-916.
Kop, R. H. J. and R. Sprik (1995). "Phase-sensitive interferometry with ultrashort optical pulses." *Review of Scientific Instruments* 66(12): 5459-5463.
Kramer, R. Z., J. Bella, et al. (1999). "Sequence dependent conformational variations of collagen triple-helical structure." *Nature.Structural Biology* 6(5): 454-7.
Kulkami, M. D., T. G. van Leeuwen, et al. (1998). "Velocity-estimation accuracy and frame-rate limitations in color Doppler optical coherence tomography." *Optics Letters* 23(13): 1057-1059.
Kwon, Y. H., C. S. Kim, et al. (2001). "Rate of visual field loss and long-term visual outcome in primary open-angle glaucoma." *American Journal of Ophthalmology* 132(1): 47-56.
Kwong, K. F., D. Yankelevich, et al. (1993). "400-Hz Mechanical Scanning Optical Delay-Line." *Optics Letters* 18(7): 558-560.
Landers, J., I. Goldberg, et al. (2002). "Analysis of risk factors that may be associated with progression from ocular hypertension to primary open angle glaucoma." *Clin Experiment Ophthalmogy* 30(4): 242-7.
Laszlo, A. and A. Venetianer (1998). Heat resistance in mammalian cells: Lessons and challenges. *Stress of Life*. 851: 169-178.
Laszlo, A. and A. Venetianer (1998). "Heat resistance in mammalian cells: lessons and challenges. [Review] [52 refs]." *Annals of the New York Academy of Sciences* 851: 169-78.
Laufer, J., R. Simpson, et al. (1998). "Effect of temperature on the optical properties of ex vivo human dermis and subdermis." *Physics in Medicine and Biology* 43(9): 2479-2489.
Lederer, D. E., J. S. Schuman, et al. (2003). "Analysis of macular volume in normal and glaucomatous eyes using optical coherence tomography." *American Journal of Ophthalmology* 135(6): 838-843.
Lee, P. P., Z. W. Feldman, et al. (2003). "Longitudinal prevalence of major eye diseases." *Archives of Ophthalmology* 121(9): 1303-1310.
Lehrer, M. S., T. T. Sun, et al. (1998). "Strategies of epithelial repair: modulation of stem cell and transit amplifying cell proliferation." *Journal of Cell Science* 111(Pt 19): 2867-75.
Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.
Leitgeb, R., C. K. Hitzenberger, et al. (2003). "Performance of fourier domain vs. time domain optical coherence tomography." *Optics Express* 11(8): 889-894.

(56) References Cited

OTHER PUBLICATIONS

Leitgeb, R., L. F. Schmetterer, et al. (2002). "Flow velocity measurements by frequency domain short coherence interferometry." *Proc. SPIE* 4619: 16-21.
Leitgeb, R. A., W. Drexler, et al. (2004). "Ultrahigh resolution Fourier domain optical coherence tomography." *Optics Express* 12(10): 2156-2165.
Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.
Leitgeb, R. A., L. Schmetterer, et al. (2003). "Real-time assessment of retinal ultrafast acquisition by color Doppler Fourier domain optical coherence tomography." Express 11(23): 3116-3121. blood flow with Optics.
Leitgeb, R. A., L. Schmetterer, et al. (2004). "Real-time measurement of in vitro flow by Fourier-domain color Doppler optical coherence tomography." *Optics Letters* 29 (2): 171-173.
LeRoyBrehonnet, F. and B. LeJeune (1997). "Utilization of Mueller matrix formalism to obtain optical targets depolarization and polarization properties." *Progress in Quantum Electronics* 21(2): 109-151.
Leske, M. C., A. M. Connell, et al. (1995). "Risk factors for open-angle glaucoma. The Barbados Eye Study. [see comments]." *Archives of Ophthalmology* 113(7): 918-24.
Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.
Leske, M. C., A. Heijl, et al. (1999). "Early Manifest Glaucoma Trial. Design and Baseline Data." *Ophthalmology* 106(11): 2144-2153.
Lewis, S. E., J. R. DeBoer, et al. (2005). "Sensitive, selective, and analytical improvements to a porous silicon gas sensor." *Sensors and Actuators B: Chemical* 110(1): 54-65.
Lexer, F., C. K. Hitzenberger, et al. (1999). "Dynamic coherent focus OCT with depth-independent transversal resolution." *Journal of Modern Optics* 46(3): 541-553.
Li, X., C. Chudoba, et al. (2000). "Imaging needle for optical coherence tomography." *Optics Letters* 25: 1520-1522.
Li, X., T. H. Ko, et al. (2001). "Intraluminal fiber-optic Doppler imaging catheter for structural and functional optical coherence tomography." *Optics Letters* 26: 1906-1908.
Liddington, M. I. and P. G. Shakespeare (1996). "Timing of the thermographic assessment of burns." *Burns* 22(1): 26-8.
Lindmo, T., D. J. Smithies, et al. (1998). "Accuracy and noise in optical Doppler tomography studied by Monte Carlo simulation." *Physics in Medicine and Biology* 43(10): 3045-3064.
Liu, J., X. Chen, et al. (1999). "New thermal wave aspects on burn evaluation of skin subjected to instantaneous heating." *IEEE Transactions on Biomedical Engineering* 46(4): 420-8.
Luke, D. G., R. McBride, et al. (1995). "Polarization mode dispersion minimization in fiber-wound piezoelectric cylinders." *Optics Letters* 20(24): 2550-2552.
MacNeill, B. D., I. K. Jong, et al. (2004). "Focal and multi-focal plaque distributions in patients with macrophage acute and stable presentations of coronary artery disease." *Journal of the American College of Cardiology* 44(5): 972-979.
Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.
Maitland, D. J. and J. T. Walsh, Jr. (1997). "Quantitative measurements of linear birefringence during heating of native collagen." *Lasers in Surgery & Medicine* 20 (3): 310-8.
Majaron, B., S. M. Srinivas, et al. (2000). "Deep coagulation of dermal collagen with repetitive Er : YAG laser irradiation." *Lasers in Surgery and Medicine* 26(2): 215-222.
Mansuripur, M. (1991). "Effects of High-Numerical-Aperture Focusing on the State of Polarization in Optical and Magnetooptic Data-Storage Systems." *Applied Optics* 30(22): 3154-3162.
Marshall, G. W., S. J. Marshall, et al. (1997). "The dentin substrate: structure and properties related to bonding." *Journal of Dentistry* 25(6): 441-458.
Martin, P. (1997). "Wound healing—Aiming for perfect skin regeneration." *Science* 276 (5309): 75-81.
Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.
Martinez, O. E., J. P. Gordon, et al. (1984). "Negative Group-Velocity Dispersion Using Refraction." *Journal of the Optical Society of America a-Optics Image Science and Vision* 1(10): 1003-1006.
McKinney, J. D., M. A. Webster, et al. (2000). "Characterization and imaging in optically scattering media by use of laser speckle and a variable-coherence source." *Optics Letters* 25(1): 4-6.
Miglior, S., M. Casula, et al. (2001). "Clinical ability of Heidelberg retinal tomograph examination to detect glaucomatous visual field changes." *Ophthalmology* 108 (9): 1621-7.
Milner, T. E., D. M. Goodman, et al. (1996). "Imaging laser heated subsurface chromophores in biological materials: Determination of lateral physical dimensions." *Physics in Medicine and Biology* 41(1): 31-44.
Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.
Milner, T. E., D. J. Smithies, et al. (1996). "Depth determination of chromophores in human skin by pulsed photothermal radiometry." *Applied Optics* 35(19): 3379-3385.
Mishchenko, M. I. and J. W. Hovenier (1995). "Depolarization of Light Backscattered by Randomly Oriented Nonspherical Particles." *Optics Letters* 20(12): 1356-&.
Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.
Mitsui, T. (1999). "High-speed detection of ballistic photons propagating through suspensions using spectral interferometry." *Japanese Journal of Applied Physics Part 1—Regular Papers Short Notes & Review Papers* 38(5A): 2978-2982.
Molteno, A. C., N. J. Bosma, et al. (1999). "Otago glaucoma surgery outcome study: long-term results of trabeculectomy—1976 to 1995." *Ophthalmology* 106(9): 1742-50.
Morgner, U., W. Drexler, et al. (2000). "Spectroscopic optical coherence tomography." *Optics Letters* 25(2): 111-113.
Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.
Mourant, J. R., A. H. Hielscher, et al. (1998). "Evidence of intrinsic differences in the light scattering properties of tumorigenic and nontumorigenic cells." *Cancer Cytopathology* 84(6): 366-374.
Muller, M., J. Squier, et al. (1998). "Dispersion pre-compensation of 15 femtosecond optical pulses for high-numerical-aperture objectives." *Journal of Microscopy-Oxford* 191: 141-150.
Muscat, S., N. McKay, et al. (2002). "Repeatability and reproducibility of corneal thickness measurements by optical coherence tomography." *Investigative Ophthalmology & Visual Science* 43(6): 1791-5.
Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.
Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.
Nelson, J. S., K. M. Kelly, et al. (2001). "Imaging blood flow in human port-wine stain in situ and in real time using optical Doppler tomography." *Archives of Dermatology* 137(6): 741-744.

(56) References Cited

OTHER PUBLICATIONS

Newson, T. P., F. Farahi, et al. (1988). "Combined Interferometric and Polarimetric Fiber Optic Temperature Sensor with a Short Coherence Length Source." *Optics Communications* 68(3): 161-165.
November, L. J. (1993). "Recovery of the Matrix Operators in the Similarity and Congruency Transformations—Applications in Polarimetry." *Journal of the Optical Society of America a-Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678-680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multi-functional spectral-domain optical coherence tomography at 1.3 mu m." *Optics Express* 13(11): 3931-3944.
Park, D. H., J. W. Hwang, et al. (1998). "Use of laser Doppler flowmetry for estimation of the depth of burns." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.
Pircher, M., E. Gotzinger, et al. (2003). "Measurement and imaging of water concentration in human cornea with differential absorption optical coherence tomography." *Optics Express* 11(18): 2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and a confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.
Podoleanu, A. G., M. Seeger, et al. (1998). "Transversal and longitudinal images from the retina of the living eye using low coherence reflectometry." *Journal of Biomedical Optics* 3(1): 12-20.
Poole, C. D. (1988). "Statistical Treatment of Polarization Dispersion in Single-Mode Fiber." *Optics Letters* 13(8): 687-689.
Povazay, B., K. Bizheva, et al. (2002). "Submicrometer axial resolution optical coherence tomography." *Optics Letters* 27(20): 1800-1802.
Qi, B., A. P. Himmer, et al. (2004). "Dynamic focus control in high-speed optical coherence tomography based on a microelectromechanical mirror." *Optics Communications* 232(1-6): 123-128.
Radhakrishnan, S., A. M. Rollins, et al. (2001). "Real-time optical coherence tomography of the anterior segment at 1310 nm." *Archives of Ophthalmology* 119(8): 1179-1185.
Rogers, A. J. (1981). "Polarization-Optical Time Domain Reflectometry—a Technique for the Measurement of Field Distributions." *Applied Optics* 20(6): 1060-1074.
Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rollins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phanto, ehms containing densely packed scatterers." *Optics Letters* 25(4): 239-241.
Sarunic, M. V., M. A. Choma, et al. (2005). "Instantaneous complex conjugate resolved spectral domain and swept-source OCT using 3×3 fiber couplers." *Optics Express* 13(3): 957-967.
Sathyam, U. S., B. W. Colston, et al. (1999). "Evaluation of optical coherence quantitation of analytes in turbid media by use of two wavelengths." *Applied Optics* 38(10): 2097-2104.
Schmitt, J. M. (1997). "Array detection for speckle reduction in optical coherence microscopy." *Physics in Medicine and Biology* 42(7):1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a-Optics Image Science and Vision* 14(6): 1231-1242.
Schmitt, J. M., S. L. Lee, et al. (1997). "An optical coherence microscope with enhanced resolving power in thick tissue." *Optics Communications* 142(4-6): 203-207.
Schmitt, J. M., S. H. Xiang, et al. (1998). "Differential absorption imaging with optical coherence tomography." *Journal of the Optical Society of America a-Optics Image Science and Vision* 15(9): 2288-2296.
Schmitt, J. M., S. H. Xiang, et al. (1999). "Speckle in optical coherence tomography." *Journal of Biomedical Optics* 4(1): 95-105.
Schmitt, J. M., M. J. Yadlowsky, et al. Coherence Microscopy. "Subsurface Imaging of Living Skin with Optical" *Dermatology* (1995). 191(2): 93-98.
Shi, H., J. Finlay, et al. (1997). "Multiwavelength 10-GHz picosecond pulse generation from a single-stripe semiconductor diode laser." *Ieee Photonics Technology Letters* 9(11): 1439-1441.
Shi, H., I. Nitta, et al. (1999). "Demonstration of phase correlation in multiwavelength mode-locked semiconductor diode lasers." *Optics Letters* 24(4): 238-240.
Simon, R. (1982). "The Connection between Mueller and Jones Matrices of Polarization Optics." *Optics Communications* 42(5): 293-297.
Smithies, D. J., T. Lindmo, et al. (1998). "Signal attenuation and localization in optical coherence tomography studied by Monte Carlo simulation." *Physics in Medicine and Biology* 43(10): 3025-3044.
Sorin, W. V. and D. F. Gray (1992). "Simultaneous Thickness and Group Index Measurement Using Optical Low-Coherence Reflectometry." *Ieee Photonics Technology Letters* 4(1): 105-107.
Sticker, M., C. K. Hitzenberger, et al. (2001). "Quantitative differential phase measurement and imaging in transparent and turbid media by optical coherence tomography." *Optics Letters* 26(8): 518-520.

(56) References Cited

OTHER PUBLICATIONS

Sticker, M., M. Pircher, et al. (2002). "En face imaging of single cell layers by differential phase-contrast optical coherence microscopy." *Optics Letters* 27(13): 1126-1128.
Stoller, P., B. M. Kim, et al. (2002). "Polarization-dependent optical second-harmonic imaging of a rat-tail tendon." *Journal of Biomedical Optics* 7(2): 205-214.
Sun, C. S. (2003). "Multiplexing of fiber-optic acoustic sensors in a Michelson interferometer configuration." *Optics Letters* 28(12): 1001-1003.
Swanson, E. A., J. A. Izatt, et al. (1993). "In-Vivo Retinal Imaging by Optical Coherence Tomography." *Optics Letters* 18(21): 1864-1866.
Takada, K., A. Himeno, et al. (1991). "Phase-Noise and Shot-Noise Limited Operations of Low Coherence Optical-Time Domain Reflectometry." *Applied Physics Letters* 59(20): 2483-2485.
Takenaka, H. (1973). "Unified Formalism for Polarization Optics by Using Group-Theory I (Theory)." *Japanese Journal of Applied Physics* 12(2): 226-231.
Tanno, N., T. Ichimura, et al. (1994). "Optical Multimode Frequency-Domain Reflectometer." *Optics Letters* 19(8): 587-589.
Tan-no, N., T. Ichimura, et al. (1994). "Optical Multimode Frequency-Domain Reflectometer." *Optics Letters* 19(8): 587-589.
Targowski, P., M. Wojtkowski, et al. (2004). "Complex spectral OCT in human eye imaging in vivo." *Optics Communications* 229(1-6): 79-84.
Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.
Tearney, G. J., B. E. Bouma, et al. (1996). "Rapid acquisition of in vivo biological images by use of optical coherence tomography." *Optics Letters* 21(17): 1408-1410.
Tearney, G. J., B. E. Bouma, et al. (1997). "In vivo endoscopic optical biopsy with optical coherence tomography." *Science* 276(5321): 2037-2039.
Tearney, G. J., M. E. Brezinski, et al. (1996). "Catheter-based optical imaging of a human coronary artery." *Circulation* 94(11): 3013-3013.
Tearney, G. J., M. E. Brezinski, et al. (1997). "In vivo endoscopic optical biopsy with optical coherence tomography." *Science* 276(5321): 2037-9.
Tearney, G. J., M. E. Brezinski, et al. (1997). "Optical biopsy in human gastrointestinal tissue using optical coherence tomography." *American Journal of Gastroenterology* 92(10): 1800-1804.
Tearney, G. J., M. E. Brezinski, et al. (1995). "Determination of the refractive index of highly scattering human tissue by optical coherence tomography." *Optics Letters* 20(21): 2258-2260.
Tearney, G. J., I. K. Jong, et al. (2000). "Porcine coronary imaging in vivo by optical coherence tomography." *Acta Cardiologica* 55(4): 233-237.
Tearney, G. J., R. H. Webb, et al. (1998). "Spectrally encoded confocal microscopy." *Optics Letters* 23(15): 1152-1154.
Tearney, G. J., H. Yabushita, et al. (2003). "Quantification of macrophage content in atherosclerotic plaques by optical coherence tomography." *Circulation* 107(1): 113-119.
Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis for imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.
Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003). "Differential spectral interferometry: an imaging technique for biomedical applications." *Optics Letters* 28(15): 1332-1334.
Vakoc, B. J., S. H. Yun, et al. (2005). "Phase-resolved optical frequency domain imaging." *Optics Express* 13(14): 5483-5493.
van Leeuwen, T. G., M. D. Kulkarni, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.
Vargas, O., E. K. Chan, et al. (1999). "Use of an agent to reduce scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by the use of optical Doppler tomography." *Applied Optics* 36(1): 144-149.
Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 μm and 1.3 μm." *Otolaryngology-Head and Neck Surgery* 130(3): 334-338.
Yang, C., A. Wax, et al. (2001). "Phase-dispersion optical tomography." *Optics Letters* 26(10): 686-688.
Yang, C., A. Wax, et al. (2001). "Phase-referenced interferometer with subwavelength and subhertz sensitivity applied to the study of cell membrane dynamics." *Optics Letters*26(16): 1271-1273.
Yang, C. H., A. Wax, et al. (2001). "Phase-dispersion optical tomography." *Optics Letters* 26(10): 686-688.

(56) References Cited

OTHER PUBLICATIONS

Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." *Optics Communications* 208(4-6): 209-214.
Yang, V. X. D., M. L. Gordon, et al. (2003). "High speed, wide velocity dynamic range Doppler optical coherence tomography (Part I): System design, signal processing, and performance." *Optical Express* 11(7): 794-809.
Yang, V. X. D., M. L. Gordon, et al. (2003). "High speed, wide velocity dynamic range Doppler optical coherence tomography (Part II): Imaging in vivo cardiac dynamics of *Xenopus laevis.*" *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13): 424-431.
Yazdanfar, S., A. M. Rollins, et al. (2000). "Imaging and velocimetry of the human retinal circulation with color Doppler optical coherence tomography." *Optical Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Opthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." Optics Letters 28(20): 1981-1983.
Yun, S. H., G. J. Tearney, et al. (2004). "Pulsed-source and swept-source spectral-domain optical coherence tomography with reduced motion artifacts." *Optics Express* 12(23): 5614-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." Optics Letters 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas et al., "Diffusing temporal light correlation for burn diagnosis". *SPIE*, 1999, 2979:468-477.
David J. Briers, "Speckle fluctuations and biomedical optics: implications and applications", *Optical Engineering*, 1993, 32(2):277-283.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.
Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "Blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.*, 1997, 14(9):2269-2277.

(56) References Cited

OTHER PUBLICATIONS

Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23-S 27.
T. Yoshimura et al., "Statistical properties of dynamic speckles", *J. Opt. Soc. Am A.* 1986, 3(7): 1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using FT-IR microspectroscopy", *Atherosclerosis*, May 1993, 181-1930.
N. V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", *Phys. Med. Biol.* 2000 (45): 1495-1509.
S.B. Adams Jr. et al., "The use of polarization sensitive optical coherence tomography and elastography to assess connective tissue", Optical Soc. of American Washington 2002, p. 3.
Erdelyi et al. "Generation of diffraction-free beams for applications in optical microlithography", *J. Vac. Sci. Technol. B* 15 (12), Mar./Apr. 1997, pp. 287-292.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
PCT International Preliminary Report on Patentability for International Application No. PCT/US2004/038404 dated Jun. 2, 2006.
Notice of Reasons for Rejection and English translation for Japanese Patent Application No. 2002-538830.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pages 659-667.
Reid, Brian J. (2001) "p53 and Neoplastic Progression in Barrett's Esophagus" *The American Journal of Gastroenterology* vol. 96, No 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers E.J et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" *Gastrointestinal Endoscopy* vol. 49, No. 3, part 2, pp. 12-16.

(56) References Cited

OTHER PUBLICATIONS

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4. pp. 38-43.
Poneros, John M. et al. (2001) "Diagnosis of Specialized Intestinal Metaplasia by Optical Coherence Tomography" *Gastroenterology* vol. 120, pp. 7-12.
Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.
Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.
Sampliner, Richard E. (2004) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.
Vogel, Alfred et al. (2003) "Mechanisms of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209.
Anderson, R. Rox et al. (1983) "Selective Photothermolysis" Precise Microsurgery by Selective Absorption of Pulsed Radiation *Science* vol. 220, No. 4596, pp. 524-527.
Jacques, Steven L. (1993) "Role of Tissue Optics and Pulse Duration on Tissue Effects During High-Power Laser Irradiation" *Applied Optics* vol. 32, No. 13, pp. 2447-2454.
Nahen, Kester et al. (1999) "Investigations on Acosustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry A. et al (2002) "Speckle-Contrast Monitoring of Tissue Thermal Modification" *Applied Optics* vol. 41, No. 28, pp. 5989-5996.
Morelli, J.G., et al (1986) "Tunable Dye Laser (577 nm) Treatment of Port Wine Stains" *Lasers in Surgery and Medicine* vol. 6, pp. 94-99.
French, P.M.W. et al. (1993) "Continuous-wave Mode-Locked Cr.$^{\alpha}$4+: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.
Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
Fernandez, Cabrera Delia et al. "Automated detection of retinal layer structures on optical coherence tomography images", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.

(56) References Cited

OTHER PUBLICATIONS

Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Fernández, Cabrera Delia et al. "Automated detection of retinal layer structures on optical coherence tomography images", *Optics Express* vol. 13, No. 25, Oct. 4, 2005, pp. 10200-10216.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al., (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.

(56) References Cited

OTHER PUBLICATIONS

E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia -Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. Of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action mailed Oct. 1, 2008 for U.S. Appl. No. 11/955,986.
Invitation of Pay Additional Fees mailed Aug. 7, 2008 for International Application No. PCT/US2008/062354.
International Search Report and Written Opinion mailed Mar. 7, 2006 for PCT/US2005/035711.
International Search Report and Written Opinion mailed Jul. 18, 2008 for PCT/US2008/057533.
International Search Report and Written Opinion mailed Jul. 4, 2008 for PCT/US2008/051432.
Australian Examiner's Report mailed May 27, 2008 for Australian patent application No. 2003210669.
International Search Report and Written Opinion mailed Jun. 10, 2008 for PCT/US2008/051335.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion dated Mar. 23, 2006 for PCT/US2005/042408.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-μm) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.

* cited by examiner

PRIOR ART

PRIOR ART

PRIOR ART

METHODS AND SYSTEMS FOR PERFORMING ANGLE-RESOLVED FOURIER-DOMAIN OPTICAL COHERENCE TOMOGRAPHY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION(S)

This application is based upon and claims the benefit of priority from U.S. patent application Ser. No. 60/776,544, filed Feb. 24, 2006, the entire disclosure of which is incorporated herein by reference.

STATEMENT REGARDING FEDERALLY SPONSORED RESEARCH

[The invention was made with the U.S. Government support under Contract No. R01 CA103769 awarded by the National Institutes of Health. Thus, the U.S. Government has certain rights in the invention.] *This invention was made with the U.S. Government support under Grant No(s). HL076398 awarded by the National Institutes of Health. The Government has certain rights in this invention.*

FIELD OF THE INVENTION

The present invention relates to methods and systems for performing angle-resolved Fourier-domain optical coherence tomography, and more particularly to measuring spatially-resolved angular backscattering distributions from transparent and turbid samples using Fourier-domain optical coherence tomography techniques.

BACKGROUND OF THE INVENTION

Optical coherence tomography ("OCT") enables cross-sectional images of biological samples to be obtained with resolution on a scale of several microns to tens of microns, thus allowing for detailed imaging of a tissue microstructure. It has been demonstrated that Fourier-domain OCT ("FD-OCT") can provide a significantly improved sensitivity over the time-domain OCT, which enables high-speed imaging. For example, FD-OCT has been implemented in two configurations, e.g., spectral-domain OCT ("SD-OCT") and optical frequency domain imaging ("OFDI"), as described in at least one of International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004. FD-OCT has been shown to have significant potential as a tool for identifying morphological changes in many clinical contexts, including cardiovascular, gastrointestinal, and retinal imaging.

One limitation of conventional OCT systems and methods is that the backscattered light from only one angular range centered at 180 degrees is collected. The same is the case for optical coherence microscopy ("OCM") systems, in which the array detection can be used to generate en-face two-dimensional images without beam scanning. An example of one such OCM system is shown in FIG. 1, as described in E. Beaurepaire et al., "Full-field optical coherence microscopy," Optics Letters 23(4): 244-246, 1998. An acquisition of light backscattered from different angles can be implemented using a technique of angular compounding, which may reduce speckle. Speckle generally manifests itself as a checkered pattern within scattering regions of the image, and makes it more difficult to discern subtle reflectance differences in the tissue reflectance.

A method and system for acquiring backscattered light at different incident angles in the context of OCT enabling angular compounding employs path length encoding. The example of such system is shown in FIG. 2, as described in N. Iftimia et al., "Speckle reduction in optical coherence tomography by 'path length encoded' angular compounding," Journal Of Biomedical Optics 8(2): 260-263, 2003. For example, an optical glass can be placed in the imaging beam path, splitting the incident field into two or more beamlets. This optical glass causes a portion of the incident beam (beamlet 2) to experience a greater path length delay than beamlet 1. In addition, beamlet 2 illuminates the sample at a different angle than beamlet 1. As a result, multiple OCT images of the sample (each acquired at a different angle) appear simultaneously on the OCT display. While being amenable to high-speed imaging, these method and system generally do not scale appropriately to a large number of angles, and can involve a tradeoff between the spatial resolution and the number of angles acquired thereby.

Another method and system translates a right angle prism, directing light from the sample arm to different positions on the focusing lens. An example of such system is shown in FIG. 3, as described in M. Bashkansky et al., "Statistics and reduction of speckle in optical coherence tomography," Optics Letters 25(8): 545-547, 2000. In these method and system, a backscattered light at a narrow angular range centered at 180 degrees is generally collected, but the angle of incidence of the incident beam with respect to the sample normal varies with the position of the prism. Such method and system likely do not provide for (or even allow) a measurement of angular backscattering distributions. The speed at which the images can be acquired may be limited by the speed at which the prism can be translated in an oscillatory manner. In yet another method and system, detection of the OCT signals with four detectors can be performed simultaneously, which enables angular compounding for the speckle reduction. An example of such system is shown in FIG. 4, as described in J. M. Schmitt, "Array detection for speckle reduction in optical coherence microscopy," Physics In Medicine And Biology 42(7): 1427-1439, 1997. In particular, the reference beam in this system is generally not larger than the incident beam. Thus, this system may not be conducive to measurements of the angular backscattering distributions. Furthermore, while each detector element receives the light backscattered at a different angle, the solid angle subtended by the light collected for a given detector element is contained entirely within that subtended by the incident beam. The detection in this system is performed in the time domain.

In the field of light-scattering spectroscopy, it is known that the angular distributions of backscattered light generally contain information regarding the size distributions of the scattering particles within the tissue. Given the optical resolution limitations of OCT, the ability to derive robust contrast between tissues with subtle differences in reflectance properties may (in certain circumstances) utilize the measurements of the angular distributions of the backscattered light. Depth-resolved angular backscattering measurements using the low-coherence interferometry have been designed for the light-scattering measurements with high angular resolution, as shown in the arrangements of FIGS. 5(a) and 5(b), as described in A. Wax et al., "Measurement of angular distributions by use of low-coherence interferometry for light-scattering spectroscopy," Optics Letters 26(6): 322-324, 2001, and FIGS. 6(a) and 6(b), as described in J. W. Pyhtila et al., "Determining nuclear morphology using an improved angle-resolved low coherence interferometry system," Optics Express 15(25): 3474-3484, 2003.

For example, light from a low-coherence source is divided into two arms of a modified Michelson interferometer, one beam being incident on the sample (or a sample arm) and another being incident on a mirror (or a reference arm). A lens placed in the reference arm can be translated in a direction parallel to the mirror face in order to provide the selectivity for different backscattering angles in the former arm. Measurements of interfered light are generally made in either the time domain (using the arrangement shown in FIGS. 5(a) and 5(b)) or the frequency domain (using the arrangement shown in FIGS. 6(a) and 6(b)). These techniques generally do not permit simultaneous measurements of the angular backscattering distributions, and the measurement speed is likely limited by the speed at which the lens can be precisely translated. While optimized for angular, point-sampling, in-situ measurements, angle-resolved LCI in its current implementations may likely be unsuitable for in-vivo clinical imaging.

Accordingly, there is a need to overcome the deficiencies described herein above. Indeed, simultaneously measuring the light that is backscattered from multiple angles in the imaging context of the optical coherence tomography may allow for high levels of speckle reduction and additional forms of image contrast.

Accordingly, there is a need to overcome the deficiencies described herein above.

OBJECTS AND SUMMARY OF THE INVENTION

To address and/or overcome the above-described problems and/or deficiencies, exemplary embodiments of systems, apparatus and methods according to the present invention are provided for measuring spatially-resolved angular backscattering distributions from transparent and turbid samples using Fourier-domain optical coherence tomography principles. In addition, according to further exemplary embodiments of the present invention, systems and methods for utilizing the backscattering distributions are provided for performing speckle reduction and for generating image contrast.

Thus, in accordance with one exemplary embodiment of the present invention, apparatus and method are provided. In particular, at least one first electro-magnetic radiation can be received and at least one second electro-magnetic radiation within a solid angle may be forwarded to a sample. The second electro-magnetic radiation may be associated with the first electro-magnetic radiation. A plurality of third electro-magnetic radiations can be received from the sample which is associated with the second electro-magnetic radiation, and at least one portion of the third electro-magnetic radiation is provided outside a periphery of the solid angle. Signals associated with each of the third electro-magnetic radiations can be simultaneously detected, with the signals being associated with information for the sample at a plurality of depths thereof. The depths can be determined using at least one of the third electro-magnetic radiations without a need to utilize another one of the third electro-magnetic radiations.

In addition, an interference can be detected (e.g., using at least one third arrangement) between the two of the third radiations and at least one fourth radiation associated with the first radiation, and information associated with the sample can be obtained as a function of the depths within the sample based on the interference. Data associated with at least one of birefringence properties, spectroscopic properties, motion, angular back-scattering properties or elastic properties of at least one portion of the sample can be provided as a function of the signals (e.g., using at least one third arrangement). At least one image of at least one portion of the sample can be generated (e.g., using at least one third arrangement) as a function of the signals. The data associated with at least one of birefringence properties, spectroscopic properties, motion, angular back-scattering properties or elastic properties of at least one portion of the sample can also be provided as a function of the signals. The data can be contrast data associated with the image (e.g., using at least one third arrangement). Data associated with scattering characteristics of at least one portion of the sample can also be provided as a function of a combination of the signals. Further, the depths may be determined using a single one of the third electro-magnetic radiations.

According to another exemplary embodiment of the present invention, apparatus and method can provided which facilitate the production of data associated with at least one sample. For example, first information associated with signals for a plurality of electro-magnetic radiations provided from the at least one sample can be received. At least first one of the electro-magnetic radiations may be provided along a first axis, and at least second one of the electro-magnetic radiations can be provided along second axis which is different from the first axis. Data for each of the signals within at least one portion of the first information may include data for a plurality of depths within the sample. Second information associated with contrast data of at least one portion of an image for the at least one sample can be produced as a function of the first information.

In yet another exemplary embodiment o f the present invention, further apparatus and method can provided. For example, at least one first electro-magnetic radiation can be received, and at least one second electro-magnetic radiation within a solid angle can be forwarded to a sample. The second electro-magnetic radiation may be associated with the first electro-magnetic radiation. At least two of a plurality of third electro-magnetic radiations may be simultaneously received from the sample which is associated with the second electro-magnetic radiation, and at least one portion of the third electro-magnetic radiations may be provided outside a periphery of the solid angle. An interference between the at least two of the third radiations and at least one fourth radiation associated with the first radiation may be detected. Information associated with the sample can be obtained as a function of at least one depth within the sample based on the interference.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which.

Figure 1:
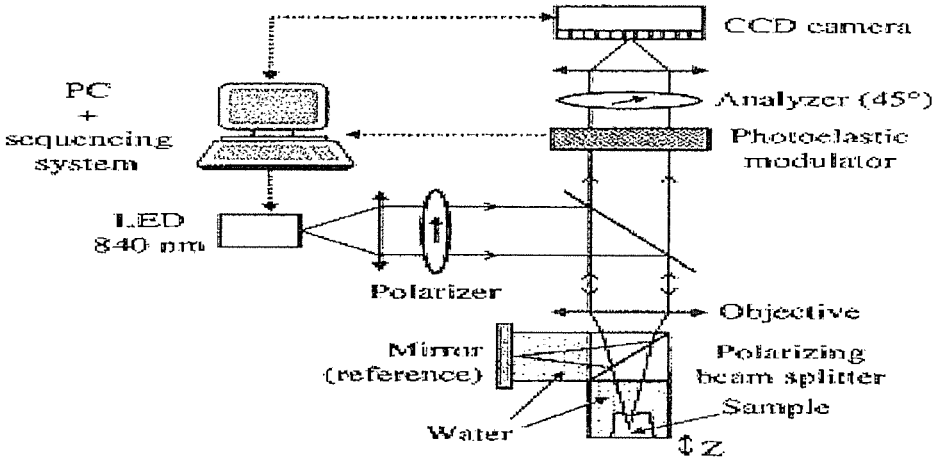
Figure 1 PRIOR ART
FIG. 1 is a block diagram of a conventional apparatus for performing Optical Coherence Microscopy ("OCM")
Figure 2:
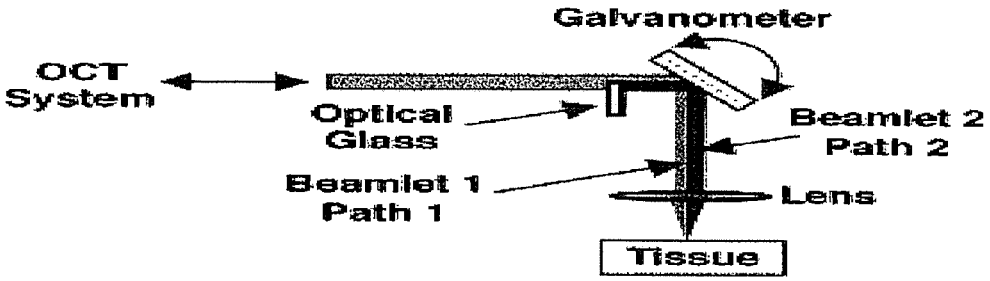
FIG. 2 is a block diagram of a conventional apparatus for performing path length encoded angular compounding for reducing speckle in Optical Coherence Tomography ("OCT")
Figure 3:
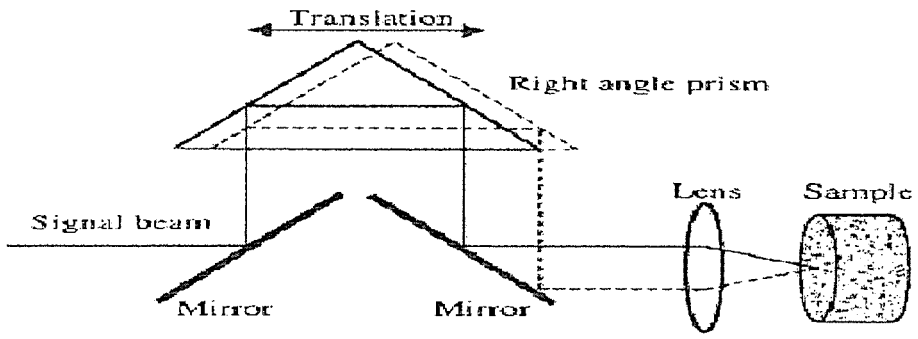
Figure 3 PRIOR ART
FIG. 3 is a block diagram of a conventional OCT apparatus for performing speckle reduction.
Figure 4:
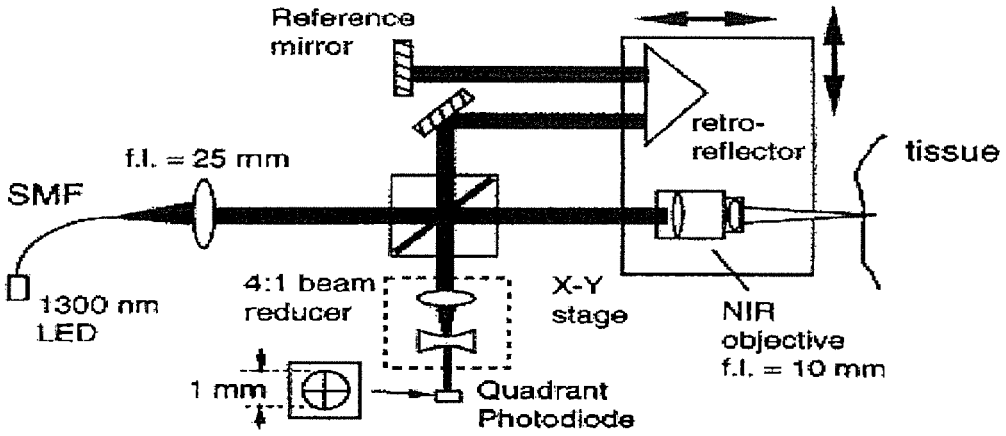
FIG. 4 is a block diagram of a conventional OCT apparatus for performing array detection for speckle reduction.
Figure 5A:
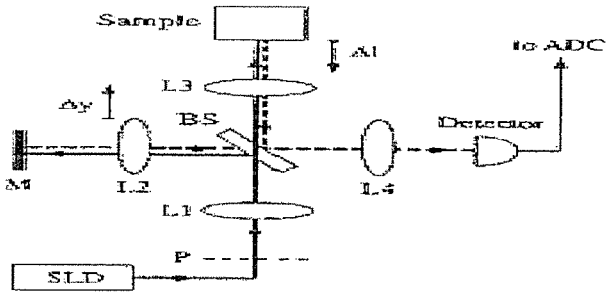
PRIOR ART Figure 5(a)
FIGS. 5(a) and 5(b) are block diagrams of conventional apparatus for performing angle-resolved low-coherence interferometry.
Figure 5B:
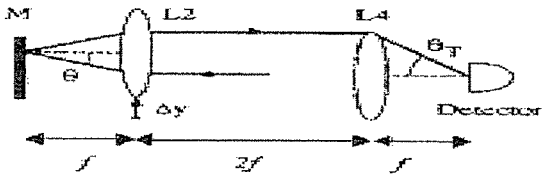
Figure 6A:
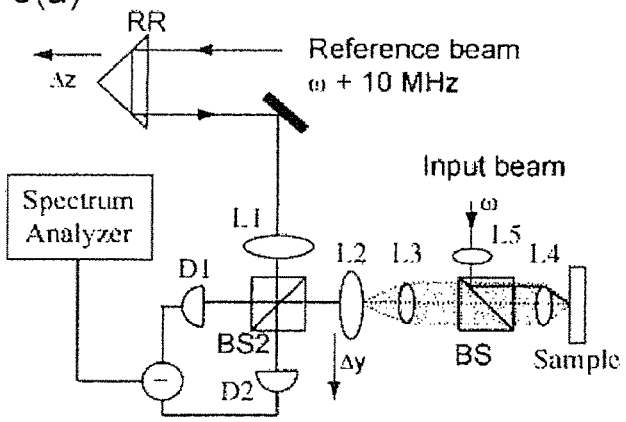
FIGS. 6(a) and 6(b) are block diagrams of further conventional apparatus for performing the angle-resolved low-coherence interferometry.
Figure 6B:
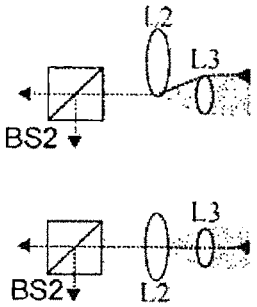

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

Exemplary Principle of Angle-Resolved FD-OCT

Angle-resolved FD-OCT is described herein below in a context of Fourier-Domain OCT. For example, in FD-OCT, the interference between reference light and the light backscattered from the imaging sample can be measured in the frequency domain in order to obtain the depth-resolved reflectance of a turbid, semi-turbid, or transparent medium. Electro-magnetic radiation (e.g., light, laser beam, etc.) of the input light source can be split into a reference beam and a sample beam. The sample beam light may be directed to the sample to be imaged, and backscattered light from the sample may be interfered with reference beam light. In the case of angle-resolved FD-OCT, the reference beam can be spatially expanded such that it can be made larger in a cross-sectional area than the cross-sectional area of the sample beam in order to allow for the interference with a range of backscattering angles beyond those subtended by the incident sample beam. The interference between the reference beam and the backscattered light can be measured using, e.g., a detector array, which may consist of (i) detectors integrated onto a single integrated circuit element, and/or (ii) individual detectors provided together in space. The angular dependence of the detected backscattered light with respect to the incident beam may be encoded in the spatial domain, as the distribution of light intensities along at least one dimension of the detector array. The wavelength dependence of the interfered light may be measured, and Fourier analysis axial reflectivity profiles corresponding to different ranges of backscattering angles can be obtained.

For example, the interference signal $S_i$ detected by an ith pixel of the detector array as a function of the frequency of laser light $v_n$ can be given by the following proportionality expression:

$$S_i(v_n) \propto P(v_n)\sqrt{\gamma_{r,i}(v_n)\gamma_{s,i}(v_n)}\int_0^\infty \sqrt{R(z)}\cos(4\pi v_n z/c + \phi(z))\,dz \quad (1)$$

where $P(v_n)$ is the total power of the source. $R(z)$ and $\phi(z)$ are the amplitude and phase terms of the reflectance profile, respectively. An axial distance z may be expressed as a relative distance, with z=0 corresponding to zero optical path difference between the sample and reference arms. The amount of the sample arm and reference arm electro-magnetic radiation (e.g., light) that reaches pixel i, expressed as fractions of $P(v_n)$ can be denoted $\gamma_{s,i}$ and $\gamma_{r,i}$, respectively.

The reflectivity profile R(z) can be obtained as the Discrete Fourier Transform of the sampled interference signal along the dimension i:

$$\sqrt{R(z)} \propto DFT(S_i) \tag{2}$$

Exemplary Principle of Speckle Reduction Using Angle-Resolved FD-OCT

Speckle results from distortions of the backscattered wavefront, which are likely caused by low-angle multiple forward scattering and diffuse multiple backscattering from closely separated refractive index heterogeneities. Angular compounding techniques are generally obtained from an observation that as a result of this interference, fields originating from different backscattering angles are de-correlated. By averaging the signals from different scattering angles incoherently, e.g., averaging of the magnitude of the reconstructed reflectance profiles, a reflectance signal with reduced speckle can be obtained.

The speckle signal-to-noise ratio ("SNR") can be a measure of the speckle reduction, as the ratio of the mean to the square-root of the variance of pixel intensities within a medium with homogenous scattering properties:

$$SNR = \frac{\langle S_k \rangle}{\sqrt{\langle (S_k - \langle S_k \rangle)^2 \rangle}}, \tag{3}$$

where the angular brackets denote an average over a collection of pixels indexed by k. The speckle SNR can be a normalized measure of the variance of the signal obtained from a homogenous sample. As such, the speckle SNR may differ from the system sensitivity, which can be defined without the presence of speckle as the minimum detectable reflectance. For the exemplary angular compounding method, the SNR may increase proportionally to the square-root of the number of uncorrelated, incoherent averages, N:

$$SNR(N)=SNR(1)\sqrt{N}. \tag{4}$$

An extent to which the SNR can be increased by angular compounding may therefore be dependent on the level of angular decorrelation. In general, higher levels of decorrelation for OCT sample volumes containing large numbers of scatterers can be obtained, as well as those at large optical depths. In comparison, sharp interfaces and scatterers with dimensions that are similar to those of the sample volumes are likely to indicate a small amount of contrast enhancement from angular compounding.

Principle of Extraction of Parameters from Angular Backscattering Distributions for Image Contrast The angular backscattering patterns of light, which may be measured by the angle-resolved FD-OCT methods and systems, can contain information about the scatterer size and the density of the imaging sample. This information may be relevant in, e.g., a clinical imaging context in order to distinguish between different regions of tissue that have very similar scattering properties that may be used in optical methods that measure the reflectance of light that is backscattered within a single angular range. Image contrast measures can be generated from angular backscattering distributions at each pixel, and such measures can be spatially smoothed, and/or image contrast measures can be generated from spatially smoothed angular backscattering distributions.

Angle-Resolved Fourier-Domain OCT

The FD-OCT techniques of SD-OCT and OFDI systems and method can measure a discrete spectral interference, and may differ in the implementation of this measurement. The OFDI systems and methods can use a wavelength-swept source to record the interference as a function of time, whereas the SD-OCT systems and methods may generally use a spectrometer to image interference spectra onto a detector array or a portion of an array.

Figure 7:
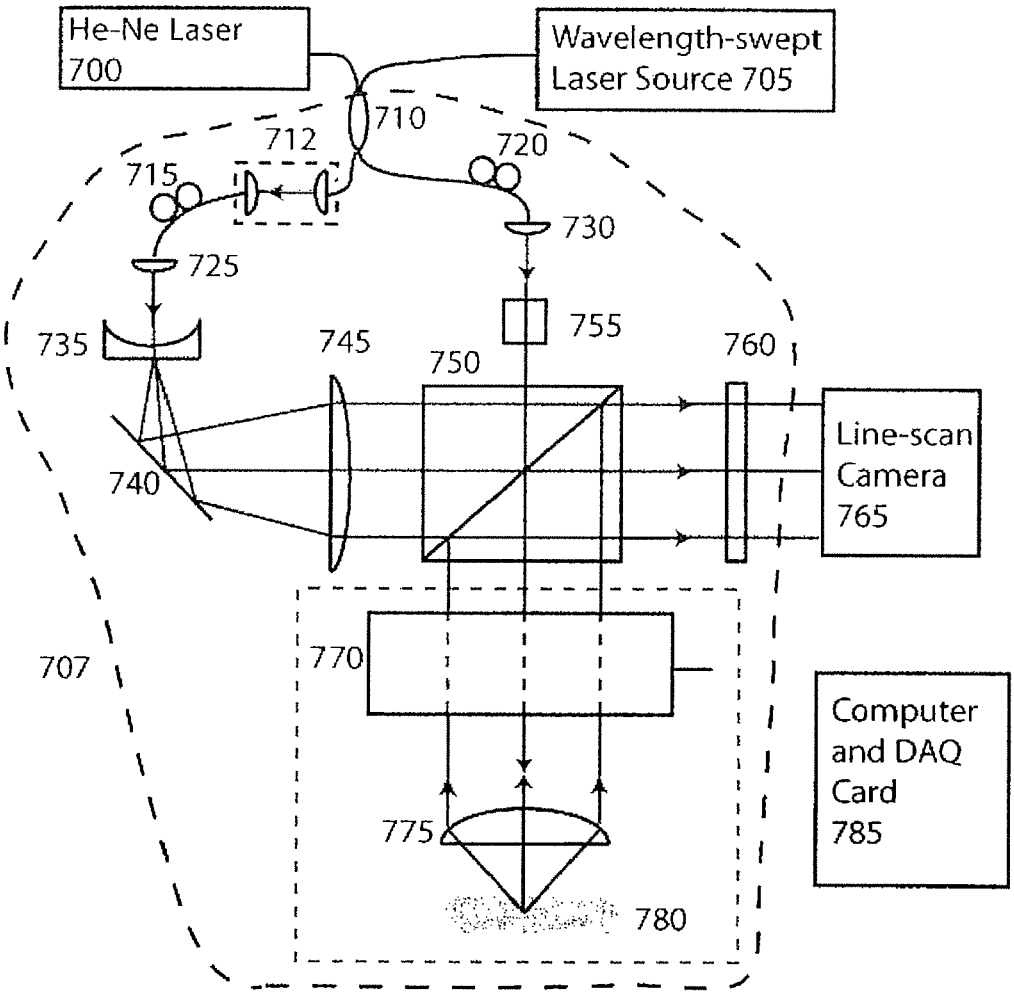
FIG. 7 is a schematic diagram of an exemplary embodiment of an angle-resolved FD-OCT system according to the present invention that employs a single-dimensional detector array, with a rectangular, gray dashed region being oriented perpendicularly to the plane of the interferometer.

FIG. 7 shows a schematic diagram of an exemplary embodiment of the angle-resolved FD-OCT imaging system in accordance with the present invention. This exemplary system can include the following modules: a wavelength-swept source 705, an interferometer 707, and an acquisition camera 765 with corresponding electronics 785. For example, the laser output can be directed to the optical coupler 710 which may split the light into two arms of the interferometer 707. A collimated light provided from a reference arm collimator 725 may be incident on a cylindrical lens telescope with elements 735, 740, 745, and this telescope can which expand the beam in the dimension of the line-scan camera 765. A free-space coupler of variable length 712 can be placed within the reference arm before the collimator 725 to facilitate reference arm length adjustments. The collimated light from the sample arm collimator 730 can be directed through a linear polarizer 755 and the beam splitter 750, where such light may be incident on imaging optics 770, 775 which focus the light on a sample 780.

Polarization controllers 715, 720 provided before the collimators 725, 730, respectively, can be positioned to maximize the fringe modulation across the frequency range of the wavelength-swept source 705. The imaging optics 770 and 775 consists of a galvanometer mirror 770 with its axis parallel to the plane of the interferometer 707 and perpendicular to the beam which is incident upon it from the beam splitter 750, and a focusing lens 775 that is placed one focal length from the sample 780. The incident beam contacts the horizontal and vertical centers of the galvanometer mirror 770. The light back-reflected from the sample 780 can pass back via the mirror 770 and the focusing lens 775, and may subsequently interfere with the reference beam at the beam splitter 750. The interfered light may be incident on a cylindrical lens 760 which focuses the light onto the line-scan camera 765. The light from a He—Ne laser 700 can be injected into the fiber coupler 710, and may act as a guide beam during the imaging procedure.

The signals from the line-scan camera 765 can be directed toward analog-to-digital (A-D) input ports of a data acquisition ("DAQ") board 785. For example, in a time period corresponding to one a-line, the DAQ board 785 can obtain m data points from n exposures, where m may be the number of detectors in the line scan camera 765, and n can be the number of frequencies sampled per a-line. The a-line acquisition rate can be determined as the quotient of the line scan camera readout rate and n. The readout from the DAQ board 785 may be synchronized to the frequency-swept laser source 705 using, e.g., TTL trigger signals by the line-scan camera 765 at the beginning of each readout phase.

Figure 8:
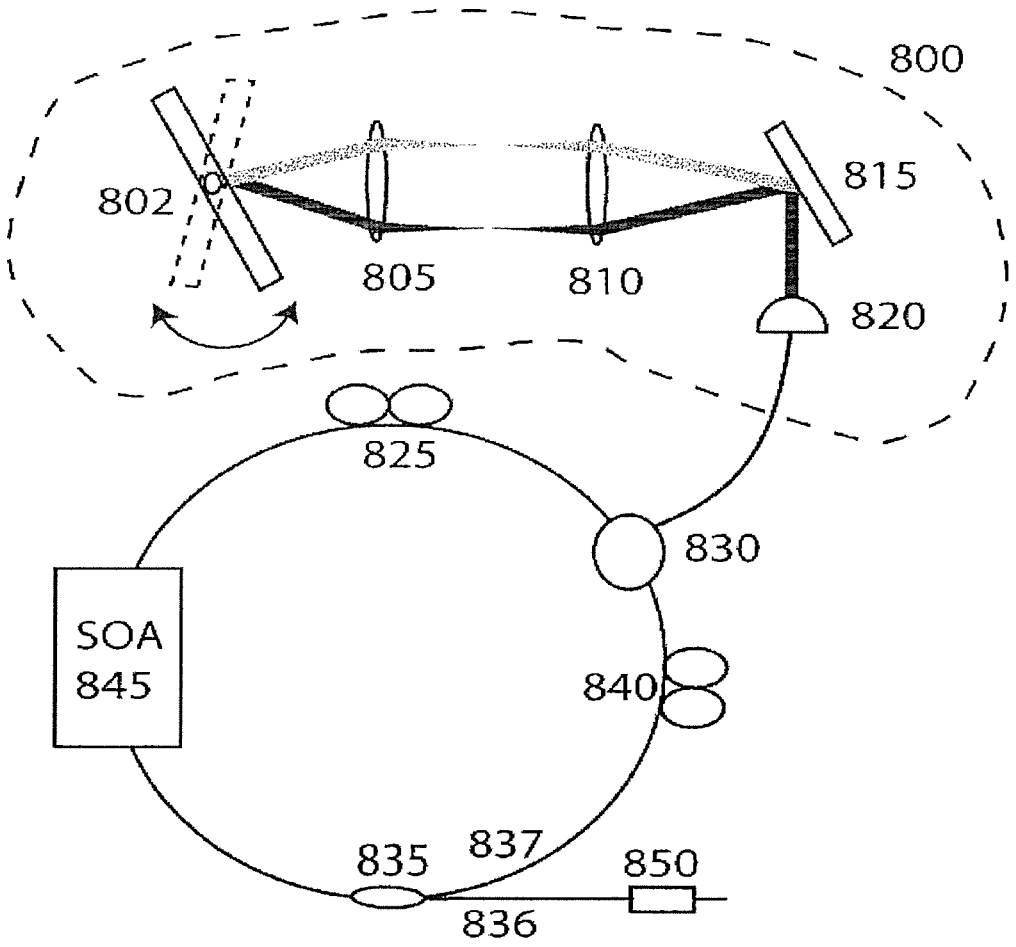
FIG. 8 is a schematic diagram of an exemplary embodiment of a wavelength-swept laser source utilized the system shown in FIG. 7.

As shown in the diagram of FIG. 8, the exemplary embodiment of the wavelength-swept source can be constructed as a ring-cavity laser with a semiconductor optical amplifier ("SOA") 845 as the gain element and a galvanometer mirror filter 800 that may include a galvanometer mirror 802, a telescope 805, 810, a diffraction grating 815, and a fiber collimator 820. Two polarization controllers 825, 840 can be provided to optimize a laser polarization and output coupler 835 which thus provides the laser output. The output coupler 835 can nominally split the light approximately equally between the output port 836 and the laser port 837. An optical circulator 830 may direct light from the laser port 837 to the galvanometer mirror filter 800 via the polarization controller 840, and can direct the light returning from the galvanometer mirror filter 800 back to the SOA 845 via the polarization controller 825. As the galvanometer mirror 802 rotates, the wavelength reflected from the galvanometer mirror filter 800 generally changes. An optical isolator 850 can be used to separate the laser from the rest of the exemplary system.

2D Detection for Resolution of Azimuthal and Polar Angles

According to a second exemplary embodiment of the present invention, the detection of the interfered light can be performed using a two dimensional array of detectors, with both dimensions corresponding to the angular distribution of backscattered light. The light incident on the sample may be provided by a wavelength-tunable, narrow line-width source. The light backscattered from the imaging sample is interfered with a reference beam that has been expanded along two spatial dimensions. Each detector array element can correspond to a unique range of polar and azimuthal angles of the backscattered light. By sweeping the laser across its tuning range, while acquiring readouts of the detector array, a vector for each discrete azimuth-polar angular pair can be obtained. Fourier-domain optical coherence tomographic reconstruction techniques may be applied the vectors, which can generate depth-resolved reflectance profiles. By scanning the beam across the sample or moving the sample relative to the beam while acquiring readouts of the array, angle-resolved reflectance profiles for different locations on the tissue may be obtained. These profiles can be combined to form two- or three-dimensional cross-sectional reflectance images.

2D Detection for Simultaneous Resolution of Angle and Wavelenth

Figure 9:
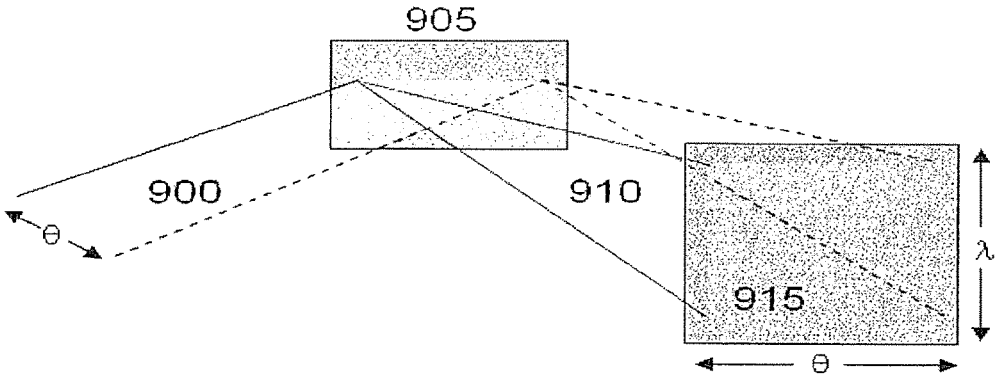
FIG. 9 is a schematic and operational diagram of a detection of the interference another exemplary embodiment of an angle-resolved FD-OCT system according to the present invention that employs a two dimensional detector array for a simultaneous detection of wavelength and angle.

According to a third exemplary embodiment of the present invention, a detection of the interfered light can be performed using, e.g., a two dimensional array of detectors, with one dimension corresponding to wavelength, and the other to the angle of the backscattered light, as shown in the operational and block diagram of FIG. 9. The light incident on the sample may be provided by a broadband source. The light backscattered from the sample can be interfered with a reference beam that has been expanded along one spatial dimension, and this dimension can correspond to the angle of the backscattered light. The interfered light 900 may be incident on a diffraction grating 905, which can separate light along another dimension corresponding to wavelength. Subsequently, this separated light 910 can be incident on the two-dimensional detector array 915. Along each one-dimensional portion of the detector array readout which corresponds to a particular backscattering angular range, Fourier-domain optical coherence tomographic reconstruction techniques can be applied to the interference spectrum, thereby providing a depth-resolved reflectance profile. By scanning the beam across the sample, or moving the sample with respect to the beam while acquiring readouts of the array, the angle-resolved reflectance profiles for different points on the tissue may be obtained. These profiles can be combined to form two- or three-dimensional cross-sectional reflectance images.

Fiber-Bundle Optical Probe

Figure 10:
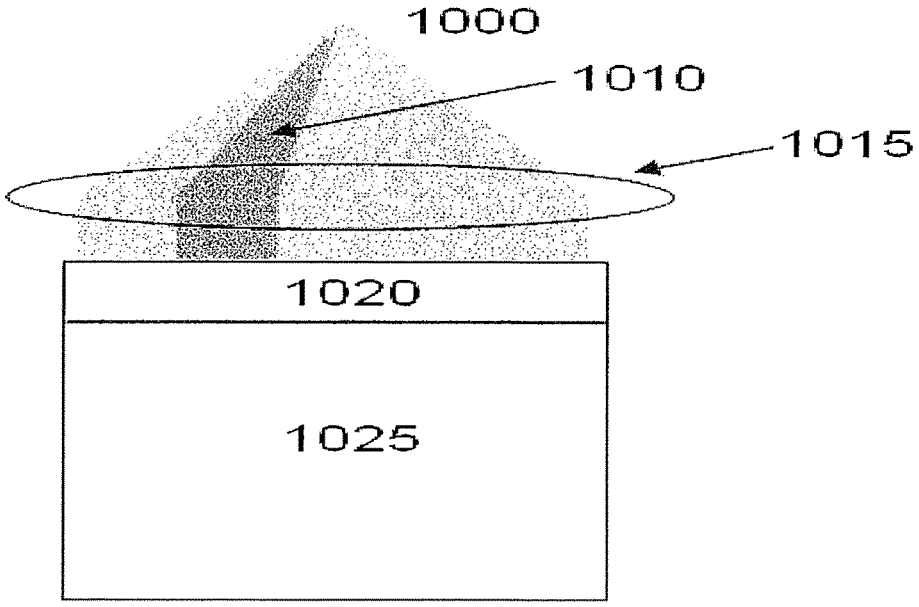
FIG. 10 is a schematic and operational diagram of imaging optics providing within a further exemplary embodiment of an angle-resolved FD-OCT system according to the present invention that can be compatible with endoscopic probes.

A fourth exemplary embodiment suitable for applications using small probe geometries in accordance with the present invention can be used with a fiber bundle, a shown in the operational and block diagram of FIG. 10. According to this exemplary embodiment, an array of optical fibers 1025 can be used to transmit and receive the light to and from an imaging sample 1000. One or more fibers in the array 1025 can be designated as "delivery fibers," through which light 1010 may be transmitted to and received from the sample 1000. Each fiber in the array 1025 can correspond to a unique, narrow range of angular backscattering angles. Lenses placed before the fibers 1020 may serve to enhance the amount of light collected by each fiber. A lens 1015 placed in front of the lenses 1020 serves to focus light onto the sample 1000, and to collimate light backscattered from the sample 1000 prior to the collection by the lenses 1020.

Polarization Sensitive Angle-Resolved FD-OCT

Polarimetric measurements in the context of optical coherence tomography may be useful for spatially resolving birefringence in biological tissue. According to a fifth exemplary embodiment according to the present invention, polarimetric measurements can be performed by one or more of the following:

a) varying the polarization of the light prior to the receipt thereof at the interferometer, and by fixing the polarization state of the reference arm and/or the sample arm;
b) varying the polarization of only the sample beam as a function of time;
c) varying the polarization of only the reference beam as a function of time;
d) varying the polarization state of one or more parts of the reference beam as a function of space, such that there may be at least two distinct parts of the reference beam that differ in the polarization state;
e) varying the polarization state of one or more parts of the backscattered light as a function of space prior to interference with the reference beam, such that there may be at least two distinct parts of the sample beam that differ in the polarization state;
f) varying the polarization state of one or more parts of the interfered light as a function of space, such that there may be at least two distinct parts that differ in the polarization state.

Using the exemplary techniques (a), (b) and/or (c), the birefringence maps of the sample can be obtained by comparing a-lines received at different times, such that the polarization states from which they originated are likely different. Using the exemplary techniques (d), (e) and/or (f), the birefringence maps of the sample can be obtained by comparing a-lines obtained from different backscattering angular ranges such that the polarization states from which they originated are likely different.

Particle Sizing

The angular frequency content obtained from the angle-resolved FD-OCT system and/or method can be analyzed using a computational framework of Mie scattering, provided that the deviations of the beam from planar waves can be accounted for in the analysis. In particular, as the angular scattering distributions which can originate from spherical dielectric scatterers may be determined using the Mie theory, the inverse problem of determining the size distributions of the scatterers from the angular scattering distributions can be performed. The Mie scattering analyses of angular backscattering distributions can enable a measurement of scatterer distributions within epithelial tissues, which may be correlated with dysplastic transitions that precede cancerous lesions.

Angular Decorrelation

Another method of processing angular backscattering distributions acquired from angle-resolved FD-OCT involves analysis of their angular frequency content. Image contrast measures include the angular frequency bin with maximum power and the width of the peak with the highest power. Analysis of the power-spectral density of the angular backscattering distributions is equivalent to analysis of the auto-correlation function by the Wiener-Kinchine theorem. The normalized auto-correlation function C can be provided by:

$$C_i = \frac{\sum_j (S_j - \langle S_j \rangle)(S_{j-i} - \langle S_j \rangle)}{\sum_j (S_j - \langle S_j \rangle)^2}. \quad (5)$$

where j and i can be angular indexes. For example, the width of the central lobe of the autocorrelation function, measured relative to the first minimum, can indicate the extent of the correlation between successive angular samples. This exemplary width can be determined for each pixel of a cross-sectional image obtained using the angle-resolved FD-OCT system and method, thus providing an image with the contrast for the de-correlation level of the angular backscattering distributions.

EXAMPLE

The exemplary embodiment of the system and method according to the present invention which can be used for reducing speckle was verified by the following experiment. Two-layer tissue phantoms were constructed from aqueous agar gel (0.5% agar by weight) and polymer microspheres of diameter 0.3 mm (Duke Scientific). The phantoms were contained in silicone isolators (Sigma). An initial scattering layer with an approximate depth of 2 mm was formed. A second scattering layer, designed to have a lower scattering coefficient than the first, was funned on top of the first and had an approximate depth of 450 mm. By analyzing the exponential signal attenuation with respect to depth, the total scattering coefficients were estimated to be 24 cm-1 and 12 cm-1 for the first and second layers, respectively.

Figure 11A:
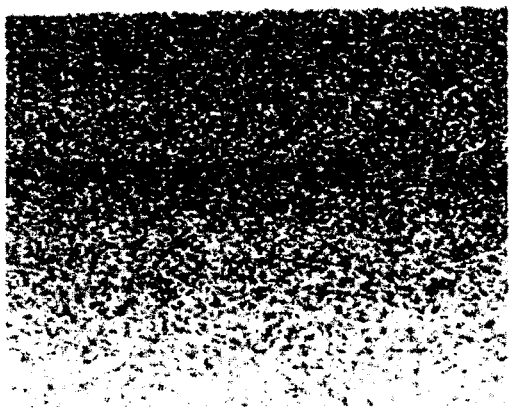
FIG. 11(a) is a two-dimensional image of a tissue phantom obtained with the exemplary embodiments of the angle-resolved FD-OCT system according to the present invention for averages across one exemplary angular sample.
Figure 11B:
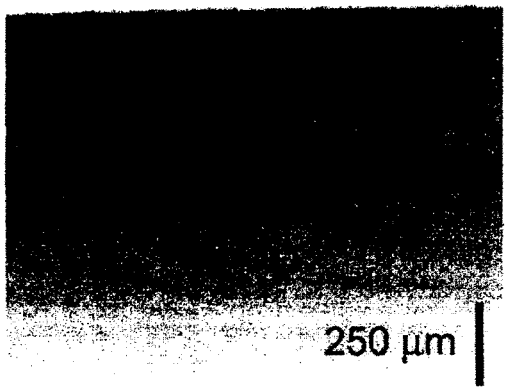
FIG. 11(b) is another two-dimensional image of the tissue phantom obtained with the exemplary embodiments of the angle-resolved FD-OCT system according to the present invention for averages across 400 angular samples.
Figure 12A:
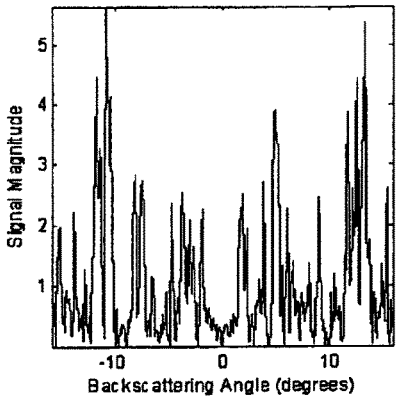
FIG. 12(a) is a graph of an angular distribution obtained from one resolution element within a tissue phantom in accordance with an exemplary embodiment of the present invention.
Figure 12B:
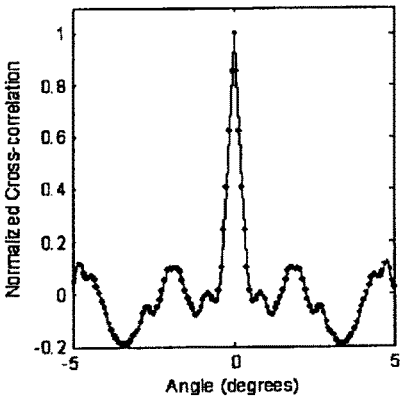
FIG. 12(b) is a graph of an angular distribution obtained from one resolution element using corresponding normalized cross-correlation function in accordance with an exemplary embodiment of the present invention.

The two-dimensional image generated from a single angular sample shows significant speckle, as shown in FIG. 11(a), in which the boundary between the two layers is not clearly visible. Speckle is greatly reduced in the angularly compounded image, with the boundary between the two layers clearly visible, as shown in FIG. 11(b). By a qualitative inspection, the resolution in the image in FIG. 11(b) is not likely to be significantly lower than that of the image of FIG. 11(a). Graphs of exemplary representative angular distributions obtained from a point that is 500 mm below the surface of the phantom and the corresponding autocorrelation function are shown in FIGS. 12(a) and 12(b).

Figure 13:
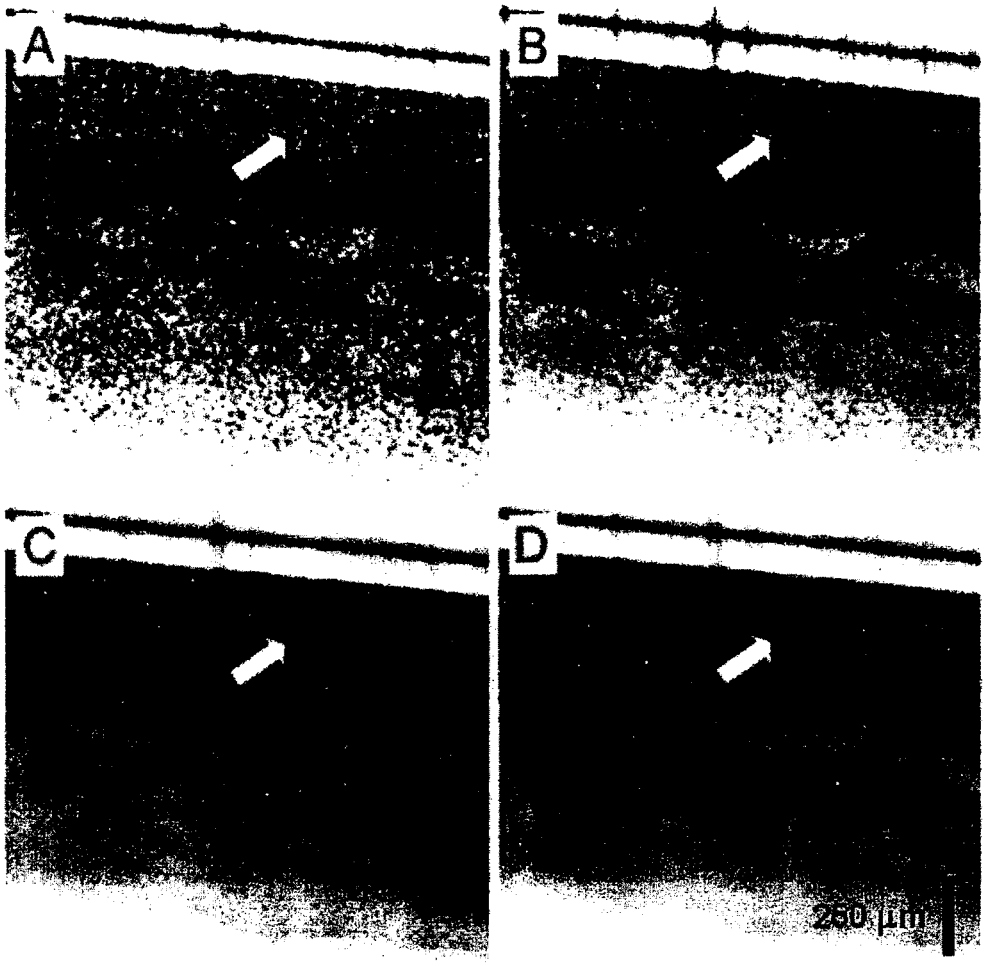
FIG. 13A is an image of an exemplary esophageal tissue obtained from compounding one angular sample, with an arrow pointing to a thin scattering layer within the epithelium.
FIG. 13B is an image of an exemplary esophageal tissue obtained from compounding three angular sample, with the arrow pointing to a thin scattering layer within the epithelium.
FIG. 13C is an image of an exemplary esophageal tissue obtained from compounding thirty (30) angular samples, with the arrow pointing to a thin scattering layer within the epithelium.
FIG. 13D is an image of an exemplary esophageal tissue obtained from compounding four hundred (400) angular samples, with the arrow pointing to a thin scattering layer within the epithelium.

The effects of angular compounding are striking when applied to esophagus tissue, as shown in the images of FIGS. 13A-13D. These images were obtained from a swine ex vivo, and the imaging sample was lightly compressed by a coverslip to enhance the visibility of the layers underlying the epithelium. In particular, as shown in FIG. 13A, the image generated from a single angular sample is qualitatively similar to that obtained by a state-of-the art conventional OFDI system, e.g., in terms of the features that are resolved and the graininess resulting from speckle. In this exemplary image, a scattering layer within the epithelium is only faintly apparent (see arrow). With three compounded angles as shown in the image of FIG. 13B, the level of speckle reduction is such that this layer can be resolved only in certain parts of the image. With 30 or more angular averages as shown in the images of FIGS. 13C and 13D, the scattering layer clearly resolved across the length of the image. Similar increases in detail afforded by angular compounding are seen within the regions of lamina propria and submucosa underlying the epithelium.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, spectral domain OCT (SD-OCT) system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus comprising:

a first arrangement *having a lens* configured to receive at least one first electro-magnetic radiation, and forward at least one second electro-magnetic radiation within a solid angle to a sample, *wherein the at least one forwarded second electro-magnetic radiation is at least one focused radiation*, wherein the at least one second electro-magnetic radiation is associated with the at least one first electro-magnetic radiation, wherein the first arrangement is configured to receive a plurality of third electro-magnetic radiations from the sample which is associated with the at least one second electro-magnetic radiation, *wherein the third electro-magnetic radiations are based on the at least one focused second electro-magnetic radiation*, and wherein *the lens receives* at least one portion of the third electro-magnetic radiations [is provided] outside a periphery of the solid angle; and a second arrangement *having a detector* configured to simultaneously detect signals which are (i) provided along optical axes associated therewith that are different from one another, and (ii) associated with each of the third electro-magnetic radiations, wherein the signals are associated with information for the at least one sample at a plurality of depths thereof, and wherein the second arrangement is configured to determine the depths using the at least one portion of the third electro-magnetic radiations.

2. The apparatus according to claim 1, [further comprising a third] *wherein the second* arrangement *having a detector* configured to detect an interference between the at least one portion of the third electro-magnetic radiation and at least one fourth electro-magnetic radiation associated with the at least one first electro-magnetic radiation, and to obtain information associated with the sample as a function of the depths within the sample based on the interference.

3. The apparatus according to claim 1, further comprising a third arrangement *having a computer* configured to provide data associated with at least one of birefringence properties, spectroscopic properties, motion, angular back-scattering properties or elastic properties of at least one portion of the sample as a function of the signals.

4. The apparatus according to claim 1, further comprising a third arrangement *having a computer* capable of generating at least one image of at least one portion of the sample as a function of the signals.

5. The apparatus according to claim 4, wherein the third arrangement is further configured to provide data associated with at least one of birefringence properties, spectroscopic properties, motion, angular back-scattering properties or elastic properties of at least one portion of the sample as a function of the signals.

6. The apparatus according to claim 5, wherein the data is contrast data associated with the at least one image.

7. The apparatus according to claim 1, further comprising a third arrangement *including a computer* configured to provide data associated with scattering characteristics of at least one portion of the sample as a function of a combination of the signals.

[8. The apparatus according to claim 1, wherein the second arrangement is configured to determine the depths using a single one of the third electro-magnetic radiations.]

[9. A method for detecting signals, comprising:

receiving at least one first electro-magnetic radiation;

forwarding at least one second electro-magnetic radiation within a solid angle to a sample, wherein the at least one second electro-magnetic radiation is associated with the at least one first electro-magnetic radiation;

receiving a plurality of third electro-magnetic radiations from the sample which is associated with the at least one second electro-magnetic radiation, wherein at least one portion of the third electro-magnetic radiations is provided outside a periphery of the solid angle;

simultaneously detecting the signals which are (i) provided along optical axes associated therewith that are different from one another, and (ii) associated with each of the third electro-magnetic radiations, wherein the signals are associated with in formation for the at least one sample at a plurality of depths thereof, and using a computer arrangement, determining the depths using the at least one portion of the third electro-magnetic radiations.]

[10. An apparatus for providing data associated with at least one sample, comprising:

a first arrangement configured to receive first information associated with signals for a plurality of electro-magnetic radiations provided from the at least one sample, wherein at least one of the electro-magnetic radiations has a frequency that changes over time, wherein at least a first one of the electro-magnetic radiations being provided along a first axis, and at least a second one of the electro-magnetic radiations being provided along a second axis which is different from the first axis, wherein data for each of the signals within at least one portion of the first information includes data for a plurality of depths within the at least one sample; and a second arrangement configured to produce second information associated with contrast data of at least one portion of an image for the at least one sample as a function of the first information.]

[11. The apparatus according to claim 10, wherein the at least one portion of the signals is provided outside a periphery of the solid angle.]

[12. The apparatus according to claim 10, wherein the second arrangement is capable of determining parameters of the least one depth within the sample using the first information.]

[13. The apparatus according to claim 10, wherein the second arrangement is capable of determining the at least one depth using data associated with a single one of the signals.]

[14. The apparatus according to claim 10, further comprising a third arrangement capable of generating at least one image of at least one portion of the sample as a function of the second information.]

[15. The apparatus according to claim 14, wherein the third arrangement is further configured to provide data associated with at least one of birefringence properties, spectroscopic properties, motion, angular back-scattering properties or elastic properties of at least one portion of the sample as a function of the second information.]

[16. The apparatus according to claim 15, wherein the data is contrast data associated with the at least one image.]

[17. The apparatus according to claim 10, further comprising a third arrangement configured to provide data associated with scattering characteristics of at least one portion of the sample as a function of a combination of the signals.]

[18. A method providing data associated with at least one sample, comprising:

receiving first information associated with signals for a plurality of electro-magnetic radiations provided from the at least one sample, wherein at least one of the electro-magnetic radiations has a frequency that changes over time, wherein at least first one of the electro-magnetic radiations being provided along a first axis, and at least second one of the electro-magnetic radiations being provided along second axis which is different from the first axis, wherein data for each of the signals within at least one portion of the first information includes data for a plurality of depths within the at least one sample; and using a computer arrangement, producing second information associated with contrast data of at least one portion of an image for the at least one sample as a function of the first information.]

19. An apparatus comprising:

a first arrangement *including a lens* configured to receive at least one first electro-magnetic radiation, and forward at least one second electro-magnetic radiation within a solid angle to a sample, *wherein the at least one forwarded second electro-magnetic radiation is at least one focused radiation*, wherein the at least one second electro-magnetic radiation is associated with the at least one first electro-magnetic radiation, wherein the first arrangement is configured to simultaneously receive at least two of a plurality of third electro-magnetic radiations from the sample which is associated with the at least one second electro-magnetic radiation, *wherein the third electro-magnetic radiations are based on the at least one focused second electro-magnetic radiation*, and wherein *the lens receives* at least one portion of the third electro-magnetic radiations [is provided] outside a periphery of the solid angle; and a second *including a detector* arrangement configured to simultaneously detect an interference between the at least two of the third radiations which are provided along optical axes associated therewith that are different from one another and at least one fourth radiation associated with the at least one first radiation, and configured to obtain information associated with the sample as a function of at least one depth within the sample based on the interference.

[20. The apparatus according to claim 19, wherein the second arrangement is configured to determine the at least one depth based on the interference.]

[21. The apparatus according to claim 19, wherein the one second arrangement is configured to simultaneously detect signals associated with each of the third electro-magnetic radiations.]

22. The apparatus according to claim [21] *19*, further comprising a third arrangement *including a computer* configured to provide data associated with a least one of birefringence properties, spectroscopic properties, motion, angular back-scattering properties or elastic properties of at least one portion of the sample as a function of the signals.

23. The apparatus according to claim [21] *19*, further comprising a third arrangement *including a computer* capable of generating at least one image of at least one portion of the sample as a function of the signals.

24. The apparatus according to claim 23, wherein the third arrangement is further configured to provide data associated with at least one of birefringence properties, spectroscopic properties, motion, angular back-scattering properties or elastic properties of at least one portion of the sample as a function of the signals.

25. The apparatus according to claim 24, wherein the data is contrast data associated with the at least one image.

26. The apparatus according to claim [21] *19*, further comprising a third arrangement *including a computer* configured to provide data associated with scattering characteristics of at least one portion of the sample as a function of a combination of the signals.

[27. The apparatus according to claim 20, wherein the second arrangement is configured to determine the depths using a single one of the third electro-magnetic radiations.]

[28. A method for detecting signals, comprising:

receiving at least one first electro-magnetic radiation;

forwarding at least one second electro-magnetic radiation within a solid angle to a sample, wherein the at least one second electro-magnetic radiation is associated with the at least one first electro-magnetic radiation;

simultaneously receiving at least two of a plurality of third electro-magnetic radiations from the sample which is associated with the at least one second electro-magnetic radiation, wherein at least one portion of the third electro-magnetic radiations is provided outside a periphery of the solid angle;

simultaneously detecting an interference between the at least two of the third radiations and at least one fourth radiation associated with the at least one first radiation, wherein the third radiations are provided along optical axes associated therewith that are different from one another; and using a computer arrangement, obtaining information associated with the sample as a function of at least one depth within the sample based on the interference.]

[29. The apparatus according to claim 1, wherein the second arrangement is further configured to combine the signals.]

[30. The method according to claim 9, further comprising, after the simultaneous detection, combining the signals.]

[31. The apparatus according to claim 10, wherein the first and second axes are optical axes.]

[32. The apparatus according to claim 10, wherein the first arrangement is at least one detector arrangement which is configured to receive the electro-magnetic radiations which are collimated.]

[33. The apparatus according to claim 32, wherein the collimated electro-magnetic radiations are provided from the same location of the at least one sample.]

[34. The method according to claim 18, wherein the first and second axes are optical axes.]

[35. The method according to claim 28, further comprising simultaneously detecting signals associated with each of the third electro-magnetic radiations which are provided along optical axes associated therewith that are different from one another.]

[36. An apparatus for providing data associated with at least one sample, comprising:

a detector arrangement configured to receive a plurality of collimated electro-magnetic radiations provided from the at least one sample and generate first information based on the collimated electro-magnetic radiations, wherein at least one of the electro-magnetic radiations has a frequency that changes over time, wherein at least a first one of the electro-magnetic radiations being received along a first axis simultaneously with at least a second one of the electro-magnetic radiations which is received along a second axis that is different from the first axis, wherein data for each of the signals within at least one portion of the first information includes data to for a plurality of depths within the at least one sample; and another arrangement configured to produce second information associated with contrast data of at least one portion of an image for the at least one sample as a function of the first information.]

[37. The apparatus according to claim 36, wherein the collimated electro-magnetic radiations are provided from the same location of the at least one sample.]

[38. A method providing data associated with at least one sample, comprising:

using a detector arrangement, receiving a plurality of collimated electro-magnetic radiations provided from the at least one sample; and generating first information based on the received collimated electro-magnetic radiations provided from the at least one sample, wherein at least one of the electro-magnetic radiations has a frequency that changes over time, wherein received along a first axis simultaneously with at least a second one of the electro-magnetic radiations which is received along a second axis that is different from the first axis, wherein data for each of the signals within at least one portion of the first information includes data for a plurality of depths within the at least one sample; and using a computer arrangement, producing second information associated with contrast data of at least one portion of an image for the at least one sample as a function of the first information.]

*39. The apparatus according to claim 1, wherein the first arrangement is an optical configuration.*

* * * * *